US006455290B1

(12) United States Patent
Berthelsen et al.

(10) Patent No.: US 6,455,290 B1
(45) Date of Patent: Sep. 24, 2002

(54) TANKYRASE HOMOLOG PROTEIN (THP), NUCLEIC ACIDS, AND METHODS RELATED TO THE SAME

(75) Inventors: Jens Berthelsen; Salvatore Toma; Antonella Isacchi, all of Milan (IT)

(73) Assignee: Pharmacia Italia S.p.A. (IT)

( * ) Notice: Subject to any disclaimer, the term of this patent is extended or adjusted under 35 U.S.C. 154(b) by 0 days.

(21) Appl. No.: 09/350,982

(22) Filed: Jul. 9, 1999

(51) Int. Cl.$^7$ .......................... C12N 9/12; C12N 1/20; C07H 21/04

(52) U.S. Cl. .................. 435/194; 435/183; 435/193; 435/252.3; 435/252.33; 435/254.11; 435/254.2; 435/255.1; 435/255.2; 435/320.1; 435/325; 435/348; 435/254; 435/357; 435/358; 435/364; 435/367; 435/369; 435/21; 530/350; 530/358; 536/23.1; 536/23.2; 536/23.5

(58) Field of Search ................................. 435/193, 194, 435/183, 252.3, 252.33, 325, 357, 254.11, 254.2, 358, 364, 367, 320, 130, 255.1, 255.2, 254.21, 348; 530/358; 536/23.1, 23.2, 23.5

(56) References Cited

U.S. PATENT DOCUMENTS

| 4,399,216 A | 8/1983 | Axel et al. ...................... 435/6 |
| 4,518,584 A | 5/1985 | Mark et al. .................... 424/85 |
| 4,683,195 A | 7/1987 | Mullis et al. .................. 435/6 |
| 4,683,202 A | 7/1987 | Mullis .......................... 435/91 |
| 4,737,462 A | 4/1988 | Mark et al. ................... 435/253 |
| 4,879,236 A | 11/1989 | Smith et al. ................ 435/235 |
| 5,874,444 A | 2/1999 | West ........................... 514/310 |

FOREIGN PATENT DOCUMENTS

| EP | 0 367 566 A | 5/1990 |
| WO | WO 91/18982 | 12/1991 |
| WO | WO 99/15647 | 4/1999 |
| WO | WO 00/61813 | 10/2000 |

OTHER PUBLICATIONS

Altschul et al., "Basic Local Alignment Search Tool," *J. Mol. Biol.*, 1990, 215, 403–410.
Altschul et al., "Gapped Blast and PSI–Blast: a new generation of protein database search programs," *Nucl. Acids Res.*, 1997, 25(17), 3389–3402.
Anderson, "Human Gene Therapy," *Science*, 1992, 256, 808–813.
Bauer et al., "A genetic enrichment for mutations constructed by oligodeoxynucleotide–directed mutagenesis," *Gene*, 1985, 37, 73–81.
Benoist et al., "In vivo sequence requirements of the SV 40 early promoter region," *Nature*, 1981, 290, 304–310.
Bowie et al., "Deciphering the Message in Protein Sequences: Tolerance to Amino Acid Substitutions," *Science*, 1990, 247, 1306–1310.

Breeden et al., "Regulation of the Yeast *HO* Gene," *Cold Spring Harbor Symp. Quant. Biol.*, 1985, 50, 643–650.
Chong et al., "A Human Telomeric Protein," *Science*, 1995, 270, 1663–1667.
Cosman et al., "High Level Stable Expression of Human Interleukin–2 Receptors in Mouse Cells Generates only Low Affinity Interleukin–2 Binding Sites," *Mol. Immunol.*, 1986, 23(9), 935–941.
Cosman et al., "Cloning, sequence and expression of human interleukin–2 receptor," *Nature*, 1984, 312, 768–771.
Craik, "Use of Oligonucleotides for Site–Specific Mutagenesis," *BioTechniques*, 1985, 12–19.
Fields et al., "A Novel genetic system to detect protein–protein interactions," *Nature*, 1989, 340, 245–246.
Goldstein, "Replicative Senescence: The Human Fibroblast Comes of Age," *Science*, 1990, 249, 1129–1133.
Greider et al., "Identification of a Specific Telomere Terminal Transferase Activity in Tetrahymena Extracts," *Cell*, 1985, 43, 405–413.
Harley et al., "Telomeres and telomerase in aging and cancer," *Curr. Opin. Genet. Dev.*, 1995, 5, 249–255.
Henikoff et al., "Amino acid substitution matrices from protein blocks," *Proc. Natl. Acad. Sci. USA*, 1992, 89, 10915–10919.
Huse et al., "Generation of a Large Combinatorial Library of the Immunoglobulin Repertoire in Phage Lambda," *Science*, 1989, 246, 1275–1281.
Karlin et al., "Applications and statistics for multiple high–scoring segments in molecular sequences," *Proc. Natl. Acad. Sci. USA*, 1993, 90, 5873–5877.
Lin, A.H. et al., "The Oxazolidinone Eperezolid Binds to the 50S Ribosomal Subunit and Competes with Binding of Chloramphenicol and Lincomycin," *Antimicrobial Agents and Chemotherapy*, 1997, 41(10), 2127–2131.
Luckow et al., "Trends in the Development of Baculovirus Expression Vectors," *Bio/Technology*, 1988, 6, 47–55.
Luckow et al., "High Level Expression of Nonfused Foreign Genes with *Autographa californica* Nuclear Polyhedrosis Virus Expression Vectors," *Virology*, 1989, 170, 31–39.
Lundblad et al., "Telomeres and Telomerase: A Simple Picture Becomes Complex," *Cell*, 1996, 87, 369–375.
Okayama et al., "A cDNA Cloning Vector that Permits Expression of cDNA Inserts in Mammanlian Cells," *Mol. Cell. Biol.*, 1983, 3(2), 280–289.
Shay et al., "A Survey of Telomerase Activity in Human Cancer," *Eur. J. Cancer*, 1997, 33(5), 787–791.

(List continued on next page.)

*Primary Examiner*—Rebecca E. Prouty
*Assistant Examiner*—Richard Hutson
(74) *Attorney, Agent, or Firm*—Woodcock Washburn LLP

(57) ABSTRACT

The present invention provides a human polypeptide homolog of human tankyrase protein (THP) and polynucleotides which identify and encode THP. In addition, the invention provides expression vectors, host cells and methods for its production. The invention also provides methods for the identification of THP agonists/antagonists, useful for the treatment of human diseases, such as human cancer and age related diseases.

27 Claims, No Drawings

OTHER PUBLICATIONS

Simonin et al., "Identification of Potential Active–site Residues in the Human Poly(ADP–ribose) Polymerase," *J. Biol. Chem.*, 1993, 268(12), 8529–8535.

Smith et al., "Comparison of Biosequences," *Adv. Appl. Math.*, 1981, 2, 482–489.

Smith et al., "Tankyrase, A Poly(ADP–Ribose) Polymerase at Human Telomeres," *Science*, 1998, 282, 1484–1487.

Summers et al., "A Manual of Methods for Baculovirus Vectors and Insect Cell Culture Procedures,"Texas Agricultural Experiment Station Bulletin No. 1555, 1987, 1–56.

van Steensell et al., "Control of telomere length by the human telomeric protein TRF1," *Nature*, 1997, 385, 740–743.

Walder et al., "Oligodeoxynucleotide–directed mutagenesis using the yeast transformation system, " *Gene*, 1986, 42, 133–139.

TANKYRASE HOMOLOG PROTEIN (THP), NUCLEIC ACIDS, AND METHODS RELATED TO THE SAME

FIELD OF THE INVENTION

The present invention is directed, in part, to nucleic acid molecules encoding tankyrase homolog protein (THP), novel THP polypeptides, and assays for screening compounds which bind to THP and/or modulate the activity of THP.

BACKGROUND OF THE INVENTION

Telomeres, the physical ends of eukaryotic chromosomes, consist of short repeated nucleotide sequences that are characteristic for all telomeric DNA, from yeast to human (see, e.g., Harley et al., *Curr. Opin. Genet. Dev.*, 1995, 5, 249). Telomeres are essential for the integrity of chromosomes (see, e.g., Lundblad et al., *Cell*, 1996, 87, 369), since DNA polymerases are incapable of replicating the very end of DNA. This replication defect affects the telomeres which are progressively shortened with each cell cycle, and as they reach a critical short length, cells will die (see, e.g. Goldstein, *Science*, 1990, 249, 1129). In some cells, telomere length is preserved by a ribonucleoprotein reverse transcriptase, referred to as "telomerase," which adds the characteristic telomere repeats (Greider et al., *Cell*, 1985, 43, 405). Telomerase is not expressed in most somatic cells and, as a consequence, these cells have a finite life-span. Extensive studies in a broad range of tumors indicate that 85–95% of all tumors cells express telomerase (see, e.g., Shay et al., *Eur. J Cancer*, 1997, 33, 787). Telomerase expression is an early event in tumor progression and is often present at the premalignant stage. Telomerase expression alone is not sufficient for tumorogenesis, but it is likely to be an essential permissive event to allow the tumor to continue to grow.

In addition to telomerase, another protein has been identified as capable of regulating telomere length, referred to as telomere repeat binding factor 1 (TRF1), that binds as a dimer to double stranded telomeric repeats (Chong et al., *Science*, 1995, 270, 1663). Overexpression of TRF1 in a telomerase-expressing cell line leads to progressive telomere shortening, whereas inhibition of TRF1 increases telomere length (van Steensell et al., *Nature*, 1997, 385, 740). TRF1 does not control the expression of telomerase itself but, rather, is thought to act by inhibiting telomerase action at the telomere termini (Smith et al., *Science*, 1998, 282, 1484).

The ability of TRF1 to bind to telomeric DNA can be inhibited by its modification through the action of an enzyme called tankyrase, which covalently modifies TRF1 by ADP-ribosylation (Smith et al., *Science*, 1998, 282, 1484). Tankyrase is a multidomain protein characterized by the presence of four distinct domains and are listed here in order from the polypeptide $NH_2$-terminus to the carboxy-terminus; HPS, ANK, SAM, and PARP. The HPS domain is a region containing homopolymeric runs of His, Pro, and Ser and has unknown function. The ANK domain contains 24 repeat units of a 33-amino acid ANK motif, as found in ankyrins. This domain is responsible for the binding of tankyrase to TRF1. The SAM domain (sterile alpha module) has unknown function but is believed to contribute to protein-protein interactions. The C-terminal catalytic active region is homologous to the active region of human Poly (ADP-Ribose) polymerase (PARP) enzymes. PARP catalyzes the formation of poly(ADP-ribose) onto a suitable protein receptor using $NAD^+$ as substrate. The present invention involves the surprising discovery of a novel polypeptide, herein designated THP, that exhibits at least one functional homology to human tankyrase, and its role as a key component, for example, in regulating telomerase activity and thereby telomere length. THP is, thus, useful in the search for novel anti-tumor agents that can modify and/or control telomere length and/or telomere maintenance. These and other aspects of the invention are described below.

SUMMARY OF THE INVENTION

The present invention is directed to, in part, isolated nucleic acid molecules comprising SEQ ID NO:3, or a fragment thereof; SEQ ID NO:4, or a fragment thereof; a nucleotide sequence complementary to at least a portion of SEQ ID NO:3 or SEQ ID NO:4; a nucleotide sequence homologous to SEQ ID NO:3 or SEQ ID NO:4, or a fragment thereof; a nucleotide sequence that encodes a polypeptide comprising SEQ ID NO:5, or a fragment thereof; or a nucleotide sequence that encodes a polypeptide comprising an amino acid sequence homologous to SEQ ID NO:5, or a fragment thereof.

The present invention is also directed to recombinant expression vectors comprising any of the nucleic acid molecules described above.

The present invention is also directed to host cells transformed with a recombinant expression vector comprising any of the nucleic acid molecules described above.

The present invention is also directed to methods of producing a polypeptide comprising SEQ ID NO:5, or a homolog or fragment thereof, by introducing a recombinant expression vector comprising any of the nucleic acid molecules described above into a compatible host cell, growing the host cell under conditions for expression of the polypeptide, and recovering the polypeptide from the host cell.

The present invention is also directed to compositions comprising any of the nucleic acid molecules described above and an acceptable carrier or diluent.

The present invention is also directed to isolated polypeptides encoded by any of the nucleic acid molecules described above.

The present invention is also directed to compositions comprising a polypeptide encoded by any of the nucleic acid molecules described above and an acceptable carrier or diluent.

The present invention is also directed to isolated antibodies which bind to an epitope on a polypeptide encoded by any of the nucleic acid molecules described above.

The present invention is also directed to kits comprising antibodies which bind to a polypeptide encoded by any of the nucleic acid molecules described above and a negative control antibody.

The present invention is also directed to methods of inducing an immune response in a mammal against a polypeptide encoded by any of the nucleic acid molecules described above by administering to the mammal an amount of the polypeptide sufficient to induce the immune response.

The present invention is also directed to methods of identifying a compound which binds to tankyrase homolog protein (THP) by contacting THP with a compound, and determining whether the compound binds THP.

The present invention is also directed to methods of identifying a compound which binds a nucleic acid molecule encoding tankyrase homolog protein (THP) by contacting THP with a compound, and determining whether the compound binds the nucleic acid molecule.

The present invention is also directed to methods of identifying a compound which modulates the activity of tankyrase homolog protein (THP) by contacting THP with a compound, and determining whether THP activity is modified.

The present invention is also directed to compounds which modulate THP activity identified by contacting THP with the compound, and determining whether the compound modifies activity of THP, binds to THP, or binds to a nucleic acid molecule encoding THP.

These and other aspects of the invention are described in greater detail below.

DETAILED DESCRIPTION OF PREFERRED EMBODIMENTS

The present invention provides, inter alia, isolated and purified polynucleotides that encode THP or a portion thereof, vectors containing these polynucleotides, host cells transformed with these vectors, processes of making THP, methods of using the above polynucleotides and vectors, isolated and purified THP, and methods of screening compounds which modulate THP activity.

Various definitions are made throughout this document. Most words have the meaning that would be attributed to those words by one skilled in the art. Words specifically defined either below or elsewhere in this document have the meaning provided in the context of the present invention as a whole and as are typically understood by those skilled in the art.

As used herein, the term "activity" refers to a variety of measurable indicia suggesting or revealing binding, either direct or indirect; affecting a response, i.e. having a measurable affect in response to some exposure or stimulus, including, for example, the affinity of a compound for directly binding a polypeptide or polynucleotide of the invention, or, for example, measurement of amounts of upstream or downstream proteins or other similar functions after some stimulus or event.

As used herein, the abbreviation in lower case (Thp) refers to a gene, cDNA, RNA or nucleic acid sequence while the upper case version (THP) refers to a protein, polypeptide, peptide, oligopeptide, or amino acid sequence.

As used herein, the term "antibody" is meant to refer to complete, intact antibodies, and Fab fragments and $F(ab)_2$ fragments thereof. Complete, intact antibodies include monoclonal antibodies such as murine monoclonal antibodies, chimeric antibodies and humanized antibodies.

As used herein, the term "binding" means the physical or chemical interaction between two proteins or compounds or associated proteins or compounds or combinations thereof. Binding includes ionic, non-ionic, Hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates.

As used herein, the term "compound" means any identifiable chemical or molecule, including, but not limited to, small molecule, peptide, protein, sugar, nucleotide, or nucleic acid, and such compound can be natural or synthetic.

As used herein, the term "complementary" refers to Watson-Crick basepairing between nucleotide units of a nucleic acid molecule.

As used herein, the term "contacting" means bringing together, either directly or indirectly, a compound into physical proximity to a polypeptide or polynucleotide of the invention. The polypeptide or polynucleotide can be in any number of buffers, salts, solutions etc. Contacting includes, for example, placing the compound into a beaker, microtiter plate, cell culture flask, or a microarray, such as a gene chip, or the like, which contains the nucleic acid molecule or polypeptide encoding THP or a fragment thereof.

As used herein, the phrase "homologous nucleotide sequence," or "homologous amino acid sequence," or variations thereof, refers to sequences characterised by a homology, at the nucleotide level or amino acid level, of at least about 60%, more preferably at least about 70%, more preferably at least about 80%, more preferably at least about 90%, and most preferably at least about 95% to the entire SEQ ID NO:3 or SEQ ID NO:4, or to at least a portion of SEQ ID NO:3 or SEQ ID NO:4 which encodes a functional domain of the encoded polypeptide, or to SEQ ID NO:5. Homologous nucleotide sequences include those sequences coding for isoforms of THP proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a THP protein of species other than humans, including, but not limited to, mammals. Homologous nucleotide sequences also include, but are not limited to, naturally occurring allelic variations and mutations of the nucleotide sequences set forth herein. A homologous nucleotide sequence does not, however, include the nucleotide sequence encoding human tankyrase. Homologous amino acid sequences include those amino acid sequences which encode conservative amino acid substitutions in SEQ ID NO:5, as well as polypeptides having tankyrase activity. A homologous amino acid sequence does not, however, include the amino acid sequence encoding human tankyrase. Percent homology is preferably determined by, for example, the Gap program (Wisconsin Sequence Analysis Package, Version 8 for Unix, Genetics Computer Group, University Research Park, Madison Wis.), using the default settings, which uses the algorithm of Smith and Waterman (*Adv. Appl. Math.*, 1981, 2, 482–489, which is incorporated herein by reference in its entirety).

As used herein, the term "isolated" nucleic acid molecule refers to a nucleic acid molecule (DNA or RNA) that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

As used herein, the terms "modulates" or "modifies" means an increase or decrease in the amount, quality, or effect of a particular activity or protein.

As used herein, the term "oligonucleotide" refers to a series of linked nucleotide residues which has a sufficient number of bases to be used in a polymerase chain reaction (PCR). This short sequence is based on (or designed from) a genomic or cDNA sequence and is used to amplify, confirm, or reveal the presence of an identical, similar or complementary DNA or RNA in a particular cell or tissue. Oligonucleotides comprise portions of a DNA sequence having at least about 10 nucleotides and as many as about 50 nucleotides, preferably about 15 to 30 nucleotides. They are chemically synthesized and may be used as probes.

As used herein, the term "probe" refers to nucleic acid sequences of variable length, preferably between at least about 10 and as many as about 6,000 nucleotides, depending on use. They are used in the detection of identical, similar, or complementary nucleic acid sequences. Longer length probes are usually obtained from a natural or recombinant source, are highly specific and much slower to hybridize than oligomers. They may be single- or double-stranded and carefully designed to have specificity in PCR, hybridization membrane-based, or ELISA-like technologies.

As used herein, the phrase "stringent hybridization conditions" or "stringent conditions" refers to conditions under which a probe, primer, or oligonucleotide will hybridize to its target sequence, but to no other sequences. Stringent conditions are sequence-dependent and will be different in different circumstances. Longer sequences hybridize specifically at higher temperatures. Generally, stringent conditions are selected to be about 5 C lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present in excess, at $T_m$, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 C for short probes, primers or oligonucleotides (e.g. 10 to 50 nucleotides) and at least about 60 C for longer probes, primers or oligonucleotides. Stringent conditions may also be achieved with the addition of destabilising agents, such as formamide.

The amino acid sequences are presented in the amino to carboxy direction, from left to right. The amino and carboxy groups are not presented in the sequence. The nucleotide sequences are presented by single strand only, in the 5' to 3' direction, from left to right. Nucleotides and amino acids are represented in the manner recommended by the IUPAC-IUB Biochemical Nomenclature Commission, or (for amino acids) by three letters code.

One aspect of the present invention is directed to nucleic acid molecules comprising novel nucleotide sequences encoding THP. The nucleic acid molecules are preferably either RNA or DNA, but may contain both RNA and DNA monomers or peptide nucleic acid monomers. The nucleic acid molecule may be single stranded or double stranded. The monomers of the nucleic acid molecules may be linked via conventional phosphodiester bonds or modified bonds, such as, for example, phosphorothioate bonds and the like. In addition, the sugar moieties of the monomers may be modified by, for example, addition of 2' substitutions which help confer nuclease resistance and/or cellular uptake.

In a preferred embodiment of the invention, the nucleic acid molecule comprises SEQ ID NO:3, which is 4512 bases in length and comprises an open reading frame (ORF) of approximately 3498 nucleotides (from about position 23 to about position 3520 within SEQ ID NO:3) which encodes human THP. Alternatively, the nucleic acid molecule comprises a fragment of SEQ ID NO:3. Preferably, the fragment comprises from about 10 to about 100 nucleotides, from about 101 to about 200 nucleotides, from about 201 to about 300 nucleotides, from about 301 to about 400 nucleotides, from about 401 to about 500 nucleotides, from about 501 to about 600 nucleotides, from about 601 to about 700 nucleotides, from about 701 to about 800 nucleotides, from about 801 to about 900 nucleotides, from about 901 to about 1000 nucleotides, from about 1001 to about 1100 nucleotides, from about 1101 to about 1200 nucleotides, from about 1201 to about 1300 nucleotides, from about 1301 to about 1400 nucleotides, from about 1401 to about 1500 nucleotides, from about 1501 to about 1600 nucleotides, from about 1601 to about 1700 nucleotides, from about 1701 to about 1800 nucleotides, from about 1801 to about 1900 nucleotides, from about 1901 to about 2000 nucleotides, from about 2001 to about 2100 nucleotides, from about 2101 to about 2200 nucleotides, from about 2201 to about 2300 nucleotides, from about 2301 to about 2400 nucleotides, from about 2401 to about 2500 nucleotides, from about 2501 to about 2600 nucleotides, from about 2601 to about 2700 nucleotides, from about 2701 to about 2800 nucleotides, from about 2801 to about 2900 nucleotides, from about 2901 to about 3000 nucleotides, from about 3001 to about 3100 nucleotides, from about 3101 to about 3200 nucleotides, from about 3201 to about 3300 nucleotides, from about 3301 to about 3400 nucleotides, from about 3401 to about 3500 nucleotides, from about 3501 to about 3600 nucleotides, from about 3601 to about 3700 nucleotides, from about 3701 to about 3800 nucleotides, from about 3801 to about 3900 nucleotides, from about 3901 to about 4000 nucleotides, from about 4001 to about 4100 nucleotides, from about 4101 to about 4200 nucleotides, from about 4201 to about 4300 nucleotides, from about 4301 to about 4400 nucleotides, from about 4401 to about 4500 nucleotides, or from about 4501 to about 4511 nucleotides, and any combinations thereof. The fragment can be located within any portion of SEQ ID NO:3.

In another preferred embodiment of the invention, the nucleic acid molecule comprises SEQ ID NO:4, which is 3498 bases in length and comprises the ORF (from about position 23 to about position 3520 within SEQ ID NO:3) described above. Alternatively, the nucleic acid molecule comprises a fragment of SEQ ID NO:4. Preferably, the fragment comprises from about 10 to about 100 nucleotides, from about 101 to about 200 nucleotides, from about 201 to about 300 nucleotides, from about 301 to about 400 nucleotides, from about 401 to about 500 nucleotides, from about 501 to about 6 00 nucleotides, from about 601 to about 700 nucleotides, from about 701 to about 800 nucleotides, from about 801 to about 900 nucleotides, from about 901 to about 1000 nucleotides, from about 1001 to about 1100 nucleotides, from about 1101 to about 1200 nucleotides, from about 1201 to about 1300 nucleotides, from about 1301 to about 1400 nucleotides, from about 1401 to about 1500 nucleotides, from about 1501 to about 1600 nucleotides, from about 1601 to about 1700 nucleotides, from about 1701 to about 1800 nucleotides, from about 1801 to about 1900 nucleotides, from about 1901 to about 2000 nucleotides, from about 2001 to about 2100 nucleotides, from about 2101 to about 2200 nucleotides, from about 2201 to about 2300 nucleotides, from about 2301 to about 2400 nucleotides, from about 2401 to about 2500 nucleotides, from about 2501 to about 2600 nucleotides, from about 2601 to about 2700 nucleotides, from about 2701 to about 2800 nucleotides, from about 2801 to about 2900 nucleotides, from about 2901 to about 3000 nucleotides, from about 3001 to about 3100 nucleotides, from about 3101 to about 3200 nucleotides, from about 3201 to about 3300 nucleotides, from about 3301 to about 3400 nucleotides, or from about 3401 to about 3497 nucleotides, and any combinations thereof The fragment can be located within any portion of SEQ ID NO:4.

In another preferred embodiment of the invention, the nucleic acid molecule comprises a nucleotide sequence complementary to at least a portion of SEQ ID NO:3 or SEQ ID NO:4. Preferably, the nucleic acid molecule comprises a nucleotide sequence complementary to the entire sequence recited in SEQ ID NO:3 or SEQ ID NO:4. Alternatively, the nucleic acid molecule comprises a nucleotide sequence complementary to a portion of SEQ ID NO:3 or SEQ ID NO:4 (i.e., complementary to any of the fragments described above). Nucleotide sequences complementary to at least a portion of SEQ ID NO:3 or SEQ ID NO:4 include, for example, oligonucleotides which hybridize under stringent hybridization conditions to at least a portion of SEQ ID NO:3 or SEQ ID NO:4. Preferred oligonucleotides comprise at least about 10 nucleotides and as many as about 50 nucleotides, preferably about 15 to 30 nucleotides. They are chemically synthesised and can be used as probes, primers, and as antisense agents.

In another preferred embodiment of the invention, the nucleic acid molecule comprises a nucleotide sequence homologous to SEQ ID NO:3 or SEQ ID NO:4. Preferably, the nucleotide sequence is at least about 75% homologous, more preferably at least about 80% homologous, more preferably at least about 90% homologous, and most preferably at least about 95% homologous to the entire SEQ ID NO:3 or SEQ ID NO:4. Alternatively, the nucleotide sequence is at least about 60% homologous, more preferably at least about 70% homologous, more preferably at least about 80% homologous, more preferably at least about 90% homologous, and most preferably at least about 95% homologous to a portion of SEQ ID NO:3 or SEQ ID NO:4 which encodes a functional domain of the polypeptide encoded thereby. In addition, a nucleotide sequence homologous to SEQ ID NO:3 or SEQ ID NO:4 also includes a fragment of the nucleotide sequence homologous to SEQ ID NO:3 or SEQ ID NO:4 of the lengths described above.

In another preferred embodiment of the invention, the nucleic acid molecule comprises a nucleotide sequence that encodes a polypeptide comprising SEQ ID NO:5. The nucleic acid molecule preferably comprises SEQ ID NO:4 or comprises SEQ ID NO:4 containing codon substitutions which reflect the degeneracy of the genetic code. As is well known in the art, because of the degeneracy of the genetic code, there are numerous other DNA and RNA molecules that can code for the same polypeptide as that encoded by SEQ ID NO:4. The present invention, therefore, contemplates these other DNA and RNA molecules which, on expression, encode the polypeptide of SEQ ID NO:5. DNA and RNA molecules other than those specifically disclosed herein characterised simply by a change in a codon for a particular amino acid, are within the scope of the present invention.

As is well known in the art, because of the degeneracy of the genetic code, there are numerous other DNA and RNA molecules that can code for the same polypeptide as that encoded by the aforementioned THP gene. The present invention, therefore, contemplates those other DNA and RNA molecules which, on expression, encode the polypeptide of SEQ ID NO:4. Having identified the amino acid residue sequence encoded by a Thp gene, and with knowledge of all triplet codons for each particular amino acid residue, it is possible to describe all such encoding RNA and DNA sequences. DNA and RNA molecules other than those specifically disclosed herein characterised simply by a change in a codon for a particular amino acid, are within the scope of this invention.

A table of amino acids and their representative abbreviations, symbols and codons is set forth below in the following Table 1.

TABLE 1

| Amino acid | Abbrev. | Symbol | Codon(s) |
|---|---|---|---|
| Alanine | Ala | A | GCA GCC GCG GCU |
| Cysteine | Cys | C | UGA UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

As is well known in the art, codons constitute triplet sequences of nucleotides in mRNA molecules and, as such, are characterised by the base uracil (U) in place of base thymidine (T) (which is present in DNA molecules). A simple change in a codon for the same amino acid residue within a polynucleotide will not change the sequence or structure of the encoded polypeptide.

Alternatively, the nucleic acid molecule comprises a nucleotide sequence that encodes a fragment of the polypeptide encoding SEQ ID NO:5. Preferably, the fragment comprises from about 5 to about 20 amino acids, from about 21 to about 40 amino acids, from about 41 to about 60 amino acids, from about 61 to about 80 amino acids, from about 81 to about 100 amino acids, from about 101 to about 120 amino acids, from about 121 to about 140 amino acids, from about 141 to about 160 amino acids, from about 161 to about 180 amino acids, from about 181 to about 200 amino acids, from about 201 to about 220 amino acids, from about 221 to about 240 amino acids, from about 241 to about 260 amino acids, from about 261 to about 280 amino acids, from about 281 to about 300 amino acids, from about 301 to about 320 amino acids, from about 321 to about 340 amino acids, from about 341 to about 360 amino acids, from about 361 to about 380 amino acids, from about 381 to about 400 amino acids, from about 401 to about 420 amino acids, from about 421 to about 440 amino acids, from about 441 to about 460 amino acids, from about 461 to about 480 amino acids, from about 481 to about 500 amino acids, from about 501 to about 520 amino acids, from about 521 to about 540 amino acids, from about 541 to about 560 amino acids, from about 561 to about 580 amino acids, from about 581 to about 600 amino acids, from about 601 to about 620 amino acids, from about 621 to about 640 amino acids, from about 641 to about 660 amino acids, from about 661 to about 680 amino acids, from about 681 to about 700 amino acids, from about 701 to about 720 amino acids, from about 721 to about 740 amino acids, from about 741 to about 760 amino acids, from about 761 to about 780 amino acids, from about 781 to about 800 amino acids, from about 801 to about 820 amino acids, from about 821 to about 840 amino acids, from about 841 to about 860 amino acids, from about 861 to about 880 amino acids, from about 881 to about 900 amino acids, from about 901 to about 920 amino acids, from about 921 to about 940 amino acids, from about 941 to about 960 amino acids, from about 961 to about 980 amino acids, from about 981 to about 1000 amino acids, from about 1001 to about 1020 amino acids, from about 1021 to about 1040 amino acids, from about 1041 to about 1060 amino acids, from about 1061 to about 1080 amino acids, from about 1081 to about 1100 amino acids, from about 1101 to about 1120 amino acids, from about 1121 to about 1140 amino acids, from about 1141 to about 1160 amino acids, or from about 1161 to about 1165 amino acids, and any combinations thereof. The fragment can be located within any portion of SEQ ID NO:5.

In another preferred embodiment of the invention, the nucleic acid molecule comprises a nucleotide sequence that encodes a polypeptide comprising an amino acid sequence homologous to SEQ ID NO:5. Alternatively, the nucleic acid molecule comprises a nucleotide sequence that encodes a fragment of the polypeptide comprising an amino acid sequence homologous to SEQ ID NO:5. Preferably, the fragment comprises from about 5 to about 20 amino acids, from about 21 to about 40 amino acids, from about 41 to about 60 amino acids, from about 61 to about 80 amino acids, from about 81 to about 100 amino acids, from about 101 to about 120 amino acids, from about 121 to about 140 amino acids, from about 141 to about 160 amino acids, from about 161 to about 180 amino acids, from about 181 to about 200 amino acids, from about 201 to about 220 amino acids, from about 221 to about 240 amino acids, from about 241 to about 260 amino acids, from about 261 to about 280 amino acids, from about 281 to about 300 amino acids, from about 301 to about 320 amino acids, from about 321 to about 340 amino acids, from about 341 to about 360 amino acids, from about 361 to about 380 amino acids, from about 381 to about 400 amino acids, from about 401 to about 420 amino acids, from about 421 to about 440 amino acids, from about 441 to about 460 amino acids, from about 461 to about 480 amino acids, from about 481 to about 500 amino acids, from about 501 to about 520 amino acids, from about 521 to about 540 amino acids, from about 541 to about 560 amino acids, from about 561 to about 580 amino acids, from about 581 to about 600 amino acids, from about 601 to about 620 amino acids, from about 621 to about 640 amino acids, from about 641 to about 660 amino acids, from about 661 to about 680 amino acids, from about 681 to about 700 amino acids, from about 701 to about 720 amino acids, from about 721 to about 740 amino acids, from about 741 to about 760 amino acids, from about 761 to about 780 amino acids, from about 781 to about 800 amino acids, from about 801 to about 820 amino acids, from about 821 to about 840 amino acids, from about 841 to about 860 amino acids, from about 861 to about 880 amino acids, from about 881 to about 900 amino acids, from about 901 to about 920 amino acids, from about 921 to about 940 amino acids, from about 941 to about 960 amino acids, from about 961 to about 980 amino acids, from about 981 to about 1000 amino acids, from about 1001 to about 1020 amino acids, from about 1021 to about 1040 amino acids, from about 1041 to about 1060 amino acids, from about 1061 to about 1080 amino acids, from about 1081 to about 1100 amino acids, from about 1101 to about 1120 amino acids, from about 1121 to about 1140 amino acids, from about 1141 to about 1160 amino acids, or from about 1161 to about 1165 amino acids, and any combinations thereof. The fragment can be located within any portion of SEQ ID NO:5.

With the knowledge of the nucleotide sequence information disclosed in the present invention, one skilled in the art can identify and obtain nucleotide sequences which encode THP from different sources (i.e., different tissues or different organisms) through a variety of means well known to the skilled artisan and disclosed by, for example, Sambrook et al., "Molecular cloning: a laboratory manual", Second Edition, Cold Spring Harbor Press, Cold Spring Harbor, N.Y. (1989), which is incorporated herein by reference in its entirety.

For example, DNA which encodes the THP may be obtained by screening of mRNA, cDNA, or genomic DNA with oligonucleotide probes generated from the Thp gene sequence information provided herein. Probes may be labeled with a detectable group, such as a fluorescent group, a radioactive atom or a chemiluminescent group in accordance with procedures known to the skilled artisan and used in conventional hybridization assays, as described by, for example, Sambrook et al.

A nucleic acid molecule comprising any of the Thp nucleotide sequences described above can alternatively be recovered by use of the polymerase chain reaction (PCR) procedure, with the PCR oligonucleotide primers produced from the nucleotide sequences provided herein. See U.S. Pat. No. 4,683,195 to Mullis et al. and U.S. Pat. No. 4,683,202 to Mullis. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotides probes to serve as primers for the template dependent, polymerase mediated replication of a desired nucleic acid molecule.

A wide variety of alternative cloning and in vitro amplification methodologies are well known to those skilled in the art. Examples of these techniques are found in, for example, Berger et al., *Guide to Molecular Cloning Techniques, Methods* in Enzymology 152 Academic Press, Inc., San Diego, Calif. (Berger), which is incorporated herein by reference in its entirety.

The nucleic acid molecules of the present invention, and fragments derived therefrom, are useful for screening for restriction fragment length polymorphism (RFLP) associated with certain disorders, as well as for genetic mapping.

Antisense oligonucleotides, or fragments of SEQ ID NO:3 or SEQ ID NO:4, or sequences complementary thereto, derived from the nucleotide sequences of the present invention encoding THP are useful as diagnostic tools for probing Thp gene expression in various tissues. For example, tissue can be probed in situ with oligonucleotide probes carrying detectable groups by conventional autoradiography techniques to investigate native expression of this enzyme or pathological conditions relating thereto. Antisense oligonucleotides are preferably directed to regulatory regions of SEQ ID NO:3 or SEQ ID NO:4 or mRNA corresponding thereto, including, but not limited to, the initiation codon, TATA box, enhancer sequences, and the like.

Automated sequencing methods were used to obtain or verify the nucleotide sequence of THP. The THP nucleotide sequences of the present invention were obtained for both DNA strands, and are believed to be 100% accurate. However, as is known in the art, nucleotide sequence obtained by automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well known in the art. An error in sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation.

Another aspect of the present invention is directed to vectors, or recombinant expression vectors, comprising any of the nucleic acid molecules described above. Vectors are used herein either to amplify DNA or RNA encoding THP and/or to express DNA which encodes THP. Preferred vectors include, but are not limited to, plasmids, phages, cosmids, viral particles or viruses, and integratable DNA fragments (i.e., fragments integratable into the host genome by homologous recombination). Preferred viral particles include, but are not limited to, adenoviruses, parvoviruses, herpesviruses, poxviruses, adeno-associated viruses, Semliki Forest viruses, vaccinia viruses, and retroviruses. Preferred expression vectors include, but are not limited to, pcDNA3 (Invitrogen) and pSVL (Pharmacia Biotech). Other expression vectors include, but are not limited to, pSPORT vectors, pGEM vectors (Promega), pPROEXvectors (LTI, Bethesda, Md.), Bluescript vectors (Stratagene), pQE vectors (Qiagen), pSE420 (Invitrogen), and pYES2 (Invitrogen).

Preferred expression vectors are replicable DNA constructs in which a DNA sequence encoding THP is operably linked to suitable control sequences capable of effecting the expression of the THP in a suitable host. DNA regions are operably linked when they are functionally related to each other. For example, a promoter is operably linked to a coding sequence if it controls the transcription of the sequence. Amplification vectors do not require expression control domains, but rather need only the ability to replicate in a host, usually conferred by an origin of replication, and a selection gene to facilitate recognition of transformants. The need for control sequences into the expression vector will vary depending upon the host selected and the transformation method chosen. Generally, control sequences include a transcriptional promoter, an optional operator sequence to control transcription, a sequence encoding suitable mRNA ribosomal binding, and sequences which control the termination of transcription and translation.

Preferred vectors preferably contain a promoter which is recognised by the host organism. The promoter sequences of the present invention may be either prokaryotic, eukaryotic or viral. Examples of suitable prokaryotic sequences include the $P_R$ and $P_L$ promoters of bacteriophage lambda (The bacteriophage Lambda, Hershey, A. D., Ed., Cold Spring Harbor Press, Cold Spring Harbor, N.Y. (1973), which is incorporated herein by reference in its entirety; Lambda II, Hendrix, R. W., Ed., Cold Spring Harbor Press, Cold Spring Harbor, N.Y. (1980), which is incorporated herein by reference in its entirety); the trp, recA, heat shock, and lacZ promoters of E. coli and the SV40 early promoter (Benoist, et al. Nature, 1981, 290, 304–310, which is incorporated herein by reference in its entirety). Additional promoters include, but are not limited to, mouse mammary tumor virus, long terminal repeat of human immunodeficiency virus, maloney virus, cytomegalovirus immediate early promoter, Epstein Barr virus, rous sarcoma virus, human actin, human myosin, human hemoglobin, human muscle creatine, and human metalothionein.

Additional regulatory sequences can also be included in preferred vectors. Preferred examples of suitable regulatory sequences are represented by the Shine-Dalgarno of the replicase gene of the phage MS-2 and of the gene cII of bacteriophage lambda. The Shine-Dalgarno sequence may be directly followed by the DNA encoding THP and result in the expression of the mature THP protein.

Moreover, suitable expression vectors can include an appropriate marker which allows the screening of the transformed host cells. The transformation of the selected host is carried out using any one of the various techniques well known to the expert in the art and described in Sambrook et al., supra.

An origin of replication can also be provided either by construction of the vector to include an exogenous origin or may be provided by the host cell chromosomal replication mechanism. If the vector is integrated into the host cell chromosome, the latter may be sufficient. Alternatively, rather than using vectors which contains viral origins of replication, one skilled in the art can transform mammalian cells by the method of co-transformation with a selectable marker and THP DNA. An example of a suitable marker is dihydrofolate reductase (DHFR) or thymidine kinase (see, U.S. Pat. No. 4,399,216).

Nucleotide sequences encoding THP may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesiderable joining, and ligation with appropriate ligases. Techniques for such manipulation are disclosed by Sambrook et al., supra and are well known in the art. Methods for construction of mammalian expression vectors are disclosed in, for example, Okayama et al., Mol. Cell. Biol., 1983, 3, 280, Cosman et al., Mol. Immunol., 1986, 23, 935, Cosman et al., Nature, 1984, 312, 768, EP-A-0367566, and WO 91/18982, each of which is incorporated herein by reference in its entirety.

Another aspect of the present invention is directed to transformed host cells having an expression vector comprising any of the nucleic acid molecules described above. Expression of the nucleotide sequence occurs when the expression vector is introduced into an appropriate host cell. Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera Escherichia, Bacillus, Salmonella, Pseudomonas, Streptomyces, and Staphylococcus.

If a eukaryotic expression vector is employed, then the appropriate host cell would be any eukaryotic cell capable of expressing the cloned sequence. Preferably, eukaryotic cells are cells of higher eukaryotes. Suitable eukaryotic cells include, but are not limited to, non-human mammalian tissue culture cells and human tissue culture cells. Preferred host cells include, but are not limited to, insect cells, HeLa cells, Chinese hamster ovary cells (CHO cells), African green monkey kidney cells (COS cells), human 293 cells, and murine 3T3 fibroblasts. Propagation of such cells in cell culture has become a routine procedure (see, Tissue Culture, Academic Press, Kruse and Patterson, eds. (1973), which is incorporated herein by reference in its entirety).

In addition, a yeast host may be employed as a host cell. Preferred yeast cells include, but are not limited to, the genera Saccharomyces, Pichia, and Kluveromyces. Preferred yeast hosts are S. cerevisiae and P. pastoris. Preferred yeast vectors can contain an origin of replication sequence from a 2T yeast plasmid, an autonomously replication sequence (ARS), a promoter region, sequences for polyadenylation, sequences for transcription termination, and a selectable marker gene. Shuttle vectors for replication in both yeast and *E. coli* are also included herein.

Alternatively, insect cells may be used as host cells. In a preferred embodiment, the polypeptides of the invention are expressed using a baculovirus expression system (see, Luckow et al., *Bio/Technology*, 1988, 6, 47, Baculovirus Expression Vectors: A Laboratory Manual, O'Rielly et al. (Eds.), W. H. Freeman and Company, New York, 1992, and U.S. Pat. No. 4,879,236, each of which is incorporated herein by reference in its entirety). In addition, the MAX-BAC™ complete baculovirus expression system (Invitrogen) can, for example, be used for production in insect cells.

Another aspect of the present invention is directed to compositions, including pharmaceutical compositions, comprising any of the nucleic acid molecules or recombinant expression vectors described above and an acceptable carrier or diluent. Preferably, the carrier or diluent is pharmaceutically acceptable. Suitable carriers are described in the most recent edition of *Remington's Pharmaceutical Sciences*, A. Osol, a standard reference text in this field, which is incorporated herein by reference in its entirety. Preferred examples of such carriers or diluents include, but are not limited to, water, saline, Ringer's solution, dextrose solution, and 5% human serum albumin. Liposomes and nonaqueous vehicles such as fixed oils may also be used. The formulations are sterilized by commonly used techniques.

Another aspect of the present invention is directed to an isolated polypeptide encoded by a nucleic acid molecule described above. In preferred embodiments of the invention, the isolated polypeptide comprises the amino acid sequence set forth in SEQ ID NO:5. Alternatively, the polypeptide is a fragment of the polypeptide encoding SEQ ID NO:5. Preferably, the fragment comprises from about 5 to about 20 amino acids, from about 21 to about 40 amino acids, from about 41 to about 60 amino acids, from about 61 to about 80 amino acids, from about 81 to about 100 amino acids, from about 101 to about 120 amino acids, from about 121 to about 140 amino acids, from about 141 to about 160 amino acids, from about 161 to about 180 amino acids, from about 181 to about 200 amino acids, from about 201 to about 220 amino acids, from about 221 to about 240 amino acids, from about 241 to about 260 amino acids, from about 261 to about 280 amino acids, from about 281 to about 300 amino acids, from about 301 to about 320 amino acids, from about 321 to about 340 amino acids, from about 341 to about 360 amino acids, from about 361 to about 380 amino acids, from about 381 to about 400 amino acids, from about 401 to about 420 amino acids, from about 421 to about 440 amino acids, from about 441 to about 460 amino acids, from about 461 to about 480 amino acids, from about 481 to about 500 amino acids, from about 501 to about 520 amino acids, from about 521 to about 540 amino acids, from about 541 to about 560 amino acids, from about 561 to about 580 amino acids, from about 581 to about 600 amino acids, from about 601 to about 620 amino acids, from about 621 to about 640 amino acids, from about 641 to about 660 amino acids, from about 661 to about 680 amino acids, from about 681 to about 700 amino acids, from about 701 to about 720 amino acids, from about 721 to about 740 amino acids, from about 741 to about 760 amino acids, from about 761 to about 780 amino acids, from about 781 to about 800 amino acids, from about 801 to about 820 amino acids, from about 821 to about 840 amino acids, from about 841 to about 860 amino acids, from about 861 to about 880 amino acids, from about 881 to about 900 amino acids, from about 901 to about 920 amino acids, from about 921 to about 940 amino acids, from about 941 to about 960 amino acids, from about 961 to about 980 amino acids, from about 981 to about 1000 amino acids, from about 1001 to about 1020 amino acids, from about 1021 to about 1040 amino acids, from about 1041 to about 1060 amino acids, from about 1061 to about 1080 amino acids, from about 1081 to about 1100 amino acids, from about 1101 to about 1120 amino acids, from about 1121 to about 1140 amino acids, from about 1141 to about 1160 amino acids, or from about 1161 to about 1165 amino acids, and any combinations thereof The fragment can be located within any portion of SEQ ID NO:5.

In another preferred embodiment of the invention, the polypeptide comprises an amino acid sequence homologous to SEQ ID NO:5 or a fragment thereof as described above. It is to be understood that the present invention includes proteins homologous to, and having essentially at least one biological property that is substantially similar to a biological property of the polypeptide. Preferably, the extent of the activity of the biological property is at least 10%, more preferably at least 20%, more preferably at least 30%, more preferably at least 40%, more preferably at least 50%, more preferably at least 60%, more preferably at least 70%, more preferably at least 80%, more preferably at least 90%, and most preferably 100% of the activity of the biological property of THP (e.g., SEQ ID NO:5). Such proteins are also called variants. This definition is intended to encompass isoforms, natural allelic variants, and splice variants of the Thp gene described herein. These variant forms may result from, for example, alternative splicing or differential expression in different tissue of the same source organism. The variant forms may be characterised by, for example, amino acid insertion(s), deletion(s) or substitution(s). In this connection, a variant form having an amino acid sequence which has at least about 70% sequence homology, at least about 80% sequence homology, preferably about 90% sequence homology, more preferably about 95% sequence homology and most preferably about 98% sequence homology to SEQ ID NO:5, is contemplated as being included in the present invention. A preferred homologous polypeptide comprises at least one conservative amino acid substitution compared to SEQ ID NO:5. Amino acid "insertions", "substitutions" or "deletions" are changes to or within an amino acid sequence. The variation allowed in a particular amino acid sequence may be experimentally determined by producing the peptide synthetically or by systematically making insertions, deletions, or substitutions of nucleotides in the Thp sequence using recombinant DNA techniques.

Alterations of the naturally occurring amino acid sequence can be accomplished by any of a number of known techniques. For example, mutations can be introduced into the polynucleotide encoding a polypeptide at particular locations by procedures well known to the skilled artisan, such as oligonucleotide-directed mutagenesis, which is described by Walder et al., *Gene*, 1986, 42, 133, Bauer et al., *Gene*, 1985, 37, 73, Craik, BioTechniques, January 1985, pp.12–19, Smith et al., Genetic Engineering: Principles and Methods, Plenum Press (1981), and U.S. Pat. Nos. 4,518, 584 and 4,737,462, each of which is incorporated herein by reference in its entirety.

Preferably, a THP variant of the present invention will exhibit substantially the biological activity of a naturally occurring THP polypeptide. By "exhibit substantially the biological activity of a naturally occurring THP polypeptide" is meant that THP variants within the scope of the invention can comprise conservatively substituted sequences, meaning that one or more amino acid residues of a THP polypeptide are replaced by different residues that do not alter the secondary and/or tertiary structure of the THP polypeptide. Such substitutions may include the replacement of an amino acid by a residue having similar physicochemical properties, such as substituting one aliphatic residue (Ile, Val, Leu or Ala) for another, or substitution between basic residues Lys and Arg, acidic residues Glu and Asp, amide residues Gln and Asn, hydroxyl residues Ser and Tyr, or aromatic residues Phe and Tyr. Further information regarding making phenotypically silent amino acid exchanges can be found in Bowie et al., *Science*, 1990, 247, 1306–1310, which is incorporated herein by reference in its entirety. Other THP variants which might retain substantially the biological activities of THP are those where amino acid substitutions have been made in areas outside functional regions of the protein.

The polypeptides to be expressed in such host cells may also be fusion proteins which include regions from heterologous proteins. Such regions may be included to allow, e.g., secretion, improved stability, or facilitated purification of the polypeptide. For example, a sequence encoding an appropriate signal peptide can be incorporated into expression vectors. A DNA sequence for a signal peptide (secretory leader) may be fused in-frame to the polynucleotide sequence so that the polypeptide is translated as a fusion protein comprising the signal peptide. A signal peptide that is functional in the intended host cell promotes extracellular secretion of the polypeptide. Preferably, the signal sequence will be cleaved from the polypeptide upon secretion of the polypeptide from the cell. Thus, preferred fusion proteins can be produced in which the N-terminus of THP is fused to a carrier peptide.

In one embodiment, the polypeptide comprises a fusion protein which includes a heterologous region used to facilitate purification of the polypeptide. Many of the available peptides used for such a function allow selective binding of the fusion protein to a binding partner. A preferred binding partner includes one or more of the IgG binding domains of protein A are easily purified to homogeneity by affinity chromatography on, for example, IgG-coupled Sepharose. Alternatively, many vectors have the advantage of carrying a stretch of histidine residues that can be expressed at the N-terminal or C-terminal end of the target protein. Thus the protein of interest can be recovered by metal chelation chromatography. A nucleotide sequence encoding a recognition site for a proteolytic enzyme such as enterokinase, factor X or, procollagenase or thrombin may immediately precede the sequence for THP to permit cleavage of the fusion protein to obtain the mature THP protein. Additional examples of fusion partners include, but are not limited to, the yeast I-factor, the honeybee melatin leader in sf9 insect cells, 6-His tag, thioredoxin tag, hemaglutinin tag, GST tag, and OmpA signal sequence tag. As will be understood by one of skill in the art, the binding partner which recognizes and binds to the peptide may be any molecule or compound including metal ions (e.g., metal affinity columns), antibodies, or fragments thereof, and any protein or peptide which binds the peptide, such as the FLAG tag.

The polypeptides of the invention can be used as antigens for raising antibodies against the same and used to screen for compounds that modulate the activity of THP. THP can also be used in compositions. Accordingly, the invention relates to THP or an antibody according to the invention for use as a medicament as well as to the use of the molecules in the manufacture of a medicament directed towards cancers or tumors, such as, for example, basal cell carcinomas. The molecule used as medicaments according to the invention may be the polypeptides or antibodies described herein as well as any novel substance identified in a screening method described herein.

In another aspect, the invention provides THP polypeptides with or without associated native pattern glycosylation, acylation, sialylation, or other post-translational modifications. THP expressed in yeast or mammalian expression systems (discussed below) may be similar to or significantly different from a native THP polypeptide in molecular weight and glycosylation pattern. Of course, expression of THP in bacterial expression systems will provide non-glycosylated THP.

Another aspect of the present invention is directed to compositions, including pharmaceutical compositions, comprising any of the polypeptides described above and an acceptable carrier or diluent. Preferably, the carrier or diluent is pharmaceutically acceptable. Compositions comprising a polypeptide, as described above, can be used to, for example, induce antibody formation and to induce an immune response for use in, for example, vaccine preparations.

Another aspect of the present invention is directed to methods of producing a polypeptide comprising SEQ ID NO:5, or a homolog or fragment thereof, comprising introducing any of the recombinant expression vectors described above into compatible host cells, growing the host cells under conditions for expression of the polypeptide, and recovering the polypeptide from the host cells. Eukaryotic systems are preferred since they provide a variety of processing mechanisms which result in, for example, glycosylation, carboxy-terminal amidation, oxidation or derivatization of certain amino acid residues, conformational control, and so forth.

The polypeptides of the present invention are preferably provided in an isolated form, are preferably substantially purified, and most preferably are purified to homogeneity. Host cells are preferably lysed and the polypeptide is recovered from the lysate of the host cells. Alternatively, the polypeptide is recovered by purifying the cell culture medium from the host cells, preferably without lysing the host cell. The polypeptides can be recovered and purified from recombinant cell cultures by well-known methods, including ammonium sulfate or ethanol precipitation, anion or cation exchange chromatography, phosphocellulose chromatography, hydrophobic interaction chromatography, affinity chromatography, hydroxylapatite chromatography and lectin chromatography.

In addition to producing these proteins by recombinant techniques, automated amino acid synthesizers may also be employed to produce THP polypeptides, or fragments a homologous protein thereof.

Another aspect of the present invention is directed to an antibody or antibodies which bind to an epitope on any of the polypeptides described herein. Preferably, the antibody binds to an epitope within SEQ ID NO:5. The antibodies according to the invention can be monoclonal or polyclonal and include individual, allelic, strain or species variants, or fragments thereof, both in their naturally occurring (full-length) forms and recombinant forms. Additionally, the antibodies are raised to the present proteins in either their native configuration or in non-native configurations. Anti-idiotypic antibodies can also be generated. Hybridomas which produce antibodies that bind to the polypeptides of the invention, and the antibodies themselves, are useful in the isolation and purification of the polypeptides. In addition, antibodies may be specific inhibitors of THP activity. Antibodies which specifically bind to the polypeptides of the invention can be used to purify the protein from natural sources using well known techniques and readily available starting materials. Such antibodies can also be used to purify the protein from material present when producing the protein by recombinant DNA methodology.

Many methods of making antibodies are known to persons skilled in the art. For techniques for preparing monoclonal antibodies, see e.g. Stiites et al (eds.), *Basic and Clinical Immunology* (4th ed), Lange Medical Publications, Los Altos, Calif., which is incorporated herein by reference in its entirety, and references cited therein. Techniques that involve selection of libraries of recombinant antibodies in phage or similar vectors are described in Huse et al., *Science*, 1989, 246, 1275–1281, which is incorporated herein by reference in its entirety. The production of antibodies and the protein structures of complete, intact antibodies, Fab fragments and F(ab)$_2$ fragments and the organization of the genetic sequences that encode such molecules are well known and are also described, for example, in Harlow, E. and D. Lane (1988) *ANTIBODIES: A Laboratory Manual*, Cold Spring Harbor Laboratory, Cold Spring Harbor, N.Y. which is incorporated herein by reference. Briefly, for example, a polypeptide of the invention is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the polypeptide, the hybridoma which produces them is cultured to produce a continuous supply of antibodies.

The present invention is also directed to kits, including pharmaceutical kits. The kits can comprise any of the THP nucleic acid molecules described above, any of the THP polypeptides described above, or any anti-THP antibody which binds to a polypeptide of the invention as described above, as well as a negative control. The kit preferably comprises additional components, such as, for example, instructions, solid support, reagents helpful for quantification, and the like.

Another aspect of the present invention is directed to methods of inducing an immune response in a mammal against a polypeptide of the invention by administering to the mammal an amount of the polypeptide sufficient to induce an immune response. The amount will be dependent on the animal species, size of the animal, and the like but can be determined by those skilled in the art.

Another aspect of the present invention is directed to methods of identifying compounds which bind to either THP or nucleic acid molecules encoding THP, comprising contacting THP, or a nucleic acid molecule encoding the same, with a compound, and determining whether the compound binds THP, or a nucleic acid molecule encoding the same. Binding can be determined by binding assays which are well known to the skilled artisan, including, but not limited to, gel-shift assays, Western blots, radiolabeled competition assay, phage-based expression cloning, co-fractionation by chromatography, co-precipitation, cross linking, interaction trap/two-hybrid analysis, southwestern analysis, ELISA, and the like, which are described in, for example, *Current Protocols in Molecular Biology*, 1999, John Wiley & Sons, NY, which is incorporated herein by reference in its entirety. The compounds to be screened include (which may include compounds which are suspected to bind THP, or a nucleic acid molecule encoding the same), but are not limited to, extracellular, intracellular, biologic or chemical origin. The THP polypeptide or polynucleotide employed in such a test may either be free in solution, attached to a solid support, borne on a cell surface or located intracellularly. One skilled in the art can, for example, measure the formation of complexes between THP and the compound being tested. Alternatively, one skilled in the art can examine the diminution in complex formation between THP and its substrate caused by the compound being tested.

Another aspect of the present invention is directed to methods of identifying compounds which modulate (i.e., increase or decrease) activity of THP comprising contacting THP with a compound, and determining whether the compound modifies activity of THP. The activity in the presence of the test compared is measured and compared to the activity in the absence of the test compound. Where the activity of the sample containing the test compound is higher than the activity in the sample lacking the test compound, the compound will have increased activity. Similarly, where the activity of the sample containing the test compound is lower than the activity in the sample lacking the test compound, the compound will have inhibited activity.

The present invention is particularly useful for screening compounds by using THP in any of a variety of drug screening techniques. The compounds to be screened include (which may include compounds which are suspected to modulate THP activity), but are not limited to, extracellular, intracellular, biologic or chemical origin. The THP polypeptide employed in such a test may be in any form, preferably, free in solution, attached to a solid support, borne on a cell surface or located intracellularly. One skilled in the art can, for example, measure the formation of complexes between THP and the compound being tested. Alternatively, one skilled in the art can examine the diminution in complex formation between THP and its substrate caused by the compound being tested.

The activity of THP polypeptide of the invention can be determined by, for example, measuring the ADP-ribosylating ability of the polypeptide in the presence and absence of the test compound (see, Simonin et al., *J. Biol Chem.*, 1993, 268, 8529, which is incorporated herein by reference in its entirety). In order to test for ADP-ribosylation activity, the polypeptide in question can be incubated with a radio-labeled substrate ($^{32}$P-NAD$^+$) and a suitable protein target (such as TRF1). Co-migration of radio-labeled product with the protein target upon gel electrophoresis would indicate a positive result for ADP-ribosylation of the protein target and hence PARP activity in the polypeptide in question. Observation of larger and variably sized ADP-ribosylated products, when the assay is run in the presence of excess $^{32}$P-NAD$^+$, would also be expected for PARP catalytic activity. Negative controls are warranted to preclude the possibility of extraneous PARP activity from sources other than the polypeptide in question (i.e., perform the assay with inactivated polypeptide or in the absence of polypeptide). Confirmation of the presence of ADP-ribose polymers on the protein target can be achieved by combination of the ADP-ribosylated product with a monoclonal antibody to poly(ADP-ribose) and subsequent detection of the antigen/antibody complex. In addition, PARP-like activity can be verified by addition of a specific PARP inhibitor (i.e., 3-arninobenzamide) to assay runs and would result in significant inhibition of ADP-ribosylation activity.

In another embodiment of the invention, the activity of THP polypeptide of the invention can be determined by, for example, measuring ANK binding. The ANK domain in tankyrase binds to TRF1 and has significant structural homology with ankyrins, proteins which are generally involved in protein-protein interactions. Both the ANK domain of tankyrase and ankyrins contain 24 tandem arrays of the ANK motif of 33 amino acids and share subtle variations, including a shorter fifth ANK copy. So called "ankyrin-repeat proteins" have significantly fewer ANK copies, emphasizing the fact that tankyrase is a true ankyrin. Amino acid sequence analysis can be a primary means of identifying an ANK functional domain in any polypeptide and various binding and immunological assays (i.e., immunoprecipitation) can potentially identify an ANK domain. In addition, TRF-1 binding assays can be performed with the polypeptides of the invention in the presence and absence of the test compound.

Other assays can be used to examine enzymatic activity including, but not limited to, photometric, radiometric, HPLC, electrochemical, and the like, which are described in, for example, *Enzyme Assays. A Practical Approach*, eds. R. Eisenthal and M. J. Danson, 1992, Oxford University Press, which is incorporated herein by reference in its entirety. Representative assays which can be used for determining an activity of THP are described in, for example, Smith et al., *Science*, 1998, 282, 1484–1487, Simonin et al., *J Biol. Chem.*, 1993, 268, 8529–8535, and U.S. Pat. No. 5,874,444, each of which is incorporated herein by reference in its entirety.

In preferred embodiments of the invention, methods of screening for compounds which modulate THP activity comprise contacting the compound with THP and assaying for the presence of a complex between the compound and THP. In such assays, THP is typically labeled. After suitable incubation, free THP is separated from that present in bound form, and the amount of free or uncomplexed label is a measure of the ability of the particular compound to bind to THP.

In another embodiment of the invention, high throughput screening for compounds having suitable binding affinity to THP is employed. Briefly, large numbers of different small peptide test compounds are synthesised on a solid substrate. The peptide test compounds are contacted with THP and washed. Bound THP is then detected by methods well known in the art.

Purified polypeptides of the invention can also be coated directly onto plates for use in the aforementioned drug screening techniques. In addition, non-neutralizing antibodies can be used to capture the protein and immobilize it on the solid support.

Other embodiments of the invention comprise using competitive screening assays in which neutralizing antibodies capable of binding a polypeptide of the invention specifically compete with a test compound for binding to the polypeptide. In this manner, the antibodies can be used to detect the presence of any peptide which shares one or more antigenic determinants with THP. Radiolabeled competitive binding studies are described in A. H. Lin et al. *Antimicrobial Agents and Chemotherapy* 1997, vol. 41, no. 10. pp. 2127–2131, the disclosure of which is incorporated herein by reference in its entirety.

In other embodiments of the invention, the polypeptides of the invention are employed as a research tool for identification, characterization and purification of interacting, regulatory proteins. Appropriate labels are incorporated into the polypeptides of the invention by various methods known in the art and the polypetides are used to capture interacting molecules. For example, molecules are incubated with the labeled polypeptides, washed to removed unbound polypeptides, and the polypeptide complex is quantified. Data obtained using different concentrations of polypeptide are used to calculate values for the number, affinity, and association of polypeptide with the protein complex.

Labeled polypeptides are also useful as reagents for the purification of molecules with which the polypeptide interacts including, but not limited to, inhibitors. In one embodiment of affinity purification, a polypeptide is covalently coupled to a chromatography column. Cells and their membranes are extracted, and various cellular subcomponents are passed over the column. Molecules bind to the column by virtue of their affinity to the polypeptide. The polypeptide-complex is recovered from the column, dissociated and the recovered molecule is subjected to protein sequencing. This amino acid sequence is then used to identify the captured molecule or to design degenerate oligonucleotides for cloning the corresponding gene from an appropriate cDNA library.

Alternatively, compounds may be identified which exhibit similar properties to THP of the invention, but which are smaller and exhibits a longer half time than THP in a human or animal body. When an organic compound is designed, a molecule according to the invention is used as a "lead" compound. The design of mimetics to known pharmaceutically active compounds is a well known approach in the development of pharmaceuticals based on such "lead" compounds. Mimetic design, synthesis and testing are generally used to avoid randomly screening a large number of molecules for a target property. Furthermore, structural data deriving from the analysis of the deduced amino acid sequences encoded by the DNAs of the present invention are useful to design new drugs, more specific and therefore with a higher pharmacological potency.

Comparison of the protein sequence of the present invention with the sequences present in all the available data bases showed a significant homology with the enzymatic PARP domain. Accordingly, computer modelling can be used to develop a putative tertiary structure of the proteins of the invention based on the available information of other PARP domain proteins. Thus, novel enzyme inhibitors based on the predicted structure of THP can be designed.

In a particular embodiment, the novel molecules identified by the screening methods according to the invention are low molecular weight organic molecules, in which case a composition or pharmaceutical composition can be prepared thereof for oral intake, such as in tablets. The compositions, or pharmaceutical compositions, comprising the nucleic acid molecules, vectors, polypeptides, antibodies and compounds identified by the screening methods described herein, can be prepared for any route of administration including, but not limited to, oral, intravenous, cutaneous, subcutaneous, nasal, intramuscular or intraperitoneal. The nature of the carrier or other ingredients will depend on the specific route of administration and particular embodiment of the invention to be administered. Examples of techniques and protocols that are useful in this context are, inter alia, found in Remington's Pharmaceutical Sciences, $16^{th}$ edition, Osol, A (ed.), 1980, which is incorporated herein by reference in its entirety.

The dosage of these low molecular weight compounds will depend on the disease state or condition to be treated and other clinical factors such as weight and condition of the human or animal and the route of administration of the compound. For treating human or animals, between approximately 0.5 mg/kg of body weight to 500 mg/kg of body weight of the compound can be administered. Therapy is typically administered at lower dosages and is continued until the desired therapeutic outcome is observed.

The present compounds and methods, including nucleic acid molecules, polypeptides, antibodies, compounds identified by the screening methods described herein, have a variety of pharmaceutical applications and may be used, for example, to treat or prevent unregulated cellular growth, such as cancer cell and tumour growth. In a particular embodiment, the present molecules are used in gene therapy. For a review of gene therapy procedures, see e.g. Anderson, *Science*, 1992, 256, 808–813, which is incorporated herein by reference in its entirety.

The invention is further illustrated by way of the following examples which are intended to elucidate the invention. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

Examples 1–3 presented below are actual whereas Examples 4–8 are prophetic.

EXAMPLES

Example 1

Identification of Homolog of Human Tankyrase

The nucleotide sequence of human tankyrase (GeneBank accession number AF082556), or the amino acid sequence deduced from it, was used as a query sequence against the LifeSeq™ Assembled database (Incyte Pharmaceuticals). This database, which contains previously identified and annotated sequences, was searched for regions of similarity using Gapped BLAST, (Altschul et al., *Nuc. Acids Res.*, 1997, 25, 3389, which is incorporated herein by reference in its entirety).

Briefly, the BLAST algorithm, which stands for Basic Local Alignment Search Tool is suitable for determining sequence similarity (Altschul et al., *J Mol. Biol.*, 1990, 215, 403–410, which is incorporated herein by reference in its entirety). Software or performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., *Proc. Natl. Acad. Sci. USA*, 1992, 89, 10915–10919, which is incorporated herein by reference in its entirety) alignments (B) of 50, expectation (E) of 10, M=5, N=4, and a comparison of both strands.

The BLAST algorithm (Karlin et al., *Proc. Natl. Acad. Sci. USA*, 1993, 90, 5873–5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a Thp gene or cDNA if the smallest sum probability in comparison of the test nucleic acid to a Thp nucleic acid is less than about 1, preferably less than about 0.1, more preferably less than about 0.01, and most preferably less than about 0.001.

Search of the LifeSeq™ Assembled database with the tankyrase nucleotide sequence as a query sequence identified a template sequence, with ID #232670.2, having a statistically significant overlapping homology to the query sequence. The sequence identified by template ID #232670.2 had not previously been found to be homologous to human tankyrase.

The overlapping similarity extended from tankyrase AF082556 residues 2565 to 4165, that compared to template 232670 residues 1 to 1589, aligning with an overall DNA sequence similarity of 70%. The deduced amino acid sequence of AF082556, residues 2565 to 4165, and template 232670, residues 1 to 1589, aligned with a similarity of 80%. The similarity overlap included residues of tankyrase encoding the two most C-terminal ANK repeats, the SAM domain, and the PARP domain. In addition, template 232670.2 contained 2310 bp of sequence 3' to the overlap, not present in the published tankyrase sequence (AF082556).

In the Incyte assembled database, the very 5' end sequence of template 232670.2 is given by Incyte clone 3206491 from Incyte library UTRSTMR01. Clone 3206491 was found to be 3697 bp long, and was sequenced filly by automated sequencing. The obtained sequence confirmed the sequence of template 232670.2 from nt. 1 to 3697.

Example 2

Cloning of Thp cDNA

To isolate a cDNA clone encoding full length THP, a DNA fragment corresponding to clone 3206491 nt 1 to 660, was used as a probe for hybridization screening of a phage cDNA library. The DNA fragment was amplified by the polymerase chain reaction (PCR) method. The PCR reaction mixture of 50 ml contained polymerase mixture (0.2 mM dNTPs, 1×PCR Buffer and 0.75 ml Expand High Fidelity Polymerase (Roche Biochemicals)), 1 µg of 3206491 plasmid, and 50 pmoles of forward primer (GAGTATTTGTTACAACACGG) (SEQ ID NO:1) and 50 pmoles of reverse primer (AATCTCCTTCAGCTCCTT) (SEQ ID NO:2). Amplification was performed in an Applied Biosystems PE2400 thermocycler, using the following program: 95 C for 15 seconds, 52 C for 30 seconds and 72 C for 90 seconds; repeated for 25 cycles. The amplified product was separated from the 3206491 plasmid by agarose gel electrophoresis, and purified by Qiaquick gel extraction kit (Qiagen).

A lambda phage library containing cDNAs isolated from human brain (Stratagene cat. #936213) cloned into lambda ZAPII phage-vector, was plated with *E. coli* XL-1 blue host, on 15 cm LB-agar plates at a density of 50,000 pfu per plate, and grown overnight at 37 C; (plated as described by Sambrook et al., supra). Phage plaques were transferred to nylon membranes (Amersham Hybond N.J.), denatured for 2 minutes in denaturation solution (0.5 M NaOH, 1.5 M NaCl), renatured for 5 minutes in renaturation solution (1 M Tris pH 7.5, 1.5 M NaCl), and washed briefly in 2×SSC (20×SSC: 3 M NaCl, 0.3 M Na-citrate). Filter membranes were dried and incubated at 80 C for 120 minutes to cross link the phage DNA to the membranes.

The membranes were hybridized with a DNA probe prepared as described above. A DNA fragment (25 ng) was labeled with a-$^{32}$P-dCTP (NEN) using Rediprime random priming (Amersham Pharmacia Biotech), according to manufacturers instructions. Labeled DNA was separated from unincorporated nucleotides by S200 spin columns (Amersham Pharmacia Biotech), denatured at 95 C for 5 minutes and kept on ice. The DNA-containing membranes (above) were pre-hybridised in 50 ml ExpressHyb (Clontech) solution at 68 C for 90 minutes. Subsequently, the labeled DNA probe was added to the hybridization solution, and the probe was left to hybridised to the membranes at 68 C for 70 minutes. The membranes were was five times in 2×SSC, 0.1% SDS at 42 C for 5 minutes each, and finally washed 30 minutes in 0.1×SSC, 0.2% SDS. Filters were exposed to Kodak XAR film (Eastman Kodak Company, Rochester, N.Y., USA) with an intensifying screen at −80 C for 16 hours. One positive colony was isolated from the plates, and replated with about 1000 pfu on a 15 cm LB plate. Plating, plaque lift to filters and hybridization were performed as described above. Four positive phage plaques were isolated form this secondary screening.

cDNA containing plasmids (pBluescript SK-) were rescued from the isolated phages by in vivo excision by culturing XL-1 blue cells co-infected with the isolated phages and with the Excision helper phage, as described by manufacturer (Stratagene). XL-blue cells containing the plasmids were plated on LB plates and grown at 37 C for 16 hours. Colonies (18) from each plate were replated on LB plates and grown. One colony from each plate was stricken onto a nylon filter in an ordered array, and the filter was placed on a LB plate to raise the colonies. The filter was then hybridized with a labeled probe as described above. Three positive colonies were selected and grown up in LB medium. Plasmid DNA was isolated from the three clones by Qiagen Midi Kit (Qiagen) according to the manufacturer's instructions. The size of the insert was determined by digesting the plasmid with the restriction enzymes NotI and SalI, which established an insert size of approximately 4500 bp. The sequence of the entire insert was determined by automated sequencing on both strands of the plasmids, and is shown in SEQ ID NO:3. The sequence contains an open reading frame from positions 23 to 3520 (SEQ ID NO:4), encoding a polypeptide (1166 amino acid residues long), as shown in SEQ ID NO:5. Plasmid containing SEQ ID NO:3 (pCF497) has been deposited with American Type Culture Collection (ATCC) on May 10, 1999 and has been given Deposit No. PTA-35.

Example 3

Northern Blot Analysis

Northern blots were performed to examine the expression of mRNA. The sense orientation oligonucleotide 5'-CCCGAGAGCTGTTCGAGGC (SEQ ID NO:6) with the antisense-orientation oligonucleotide 5'-CAATCTTTACTCTGTTATATCCT-3' (SEQ ID NO:7) were used as primers to amplify a portion of the THP cDNA sequence of SEQ ID NO:3. A fragment 606 basepairs from positions 96 to 701 long was amplified and used as a probe.

Multiple human tissue northern blot from Clontech (Human II #7767-1) were hybridized with the probe. Pre-hybridization was carried out at 42 C for 4 hours in 5×SSC, 1×Denhardt's reagent, 0.1% SDS, 50% formamide, 250 mg/ml salmon sperm DNA. Hybridization was performed overnight at 42 C in the same mixture with the addition of about $1.5 \times 10^6$ cpm/ml of labeled probe.

The probe was labeled with α-$^{32}$P-dCTP by Rediprime DNA labelling system (Amersham Pharmacia), purified on Nick Column (Amersharn Pharmacia) and added to the hybridization solution. The filters were washed several times at 42 C in 0.2×SSC, 0.1% SDS. Filters were exposed to Kodak XAR film (Eastman Kodak Company, Rochester, N.Y., USA) with intensifying screen at −80 C.

A single 7 kb mRNA is expressed in all tissues analysed, including heart, brain placenta, lung, liver, skeletal muscle, kidney and pancreas. The expression is rather constant in all tissues, except for placenta and skeletal muscle, which show an approximately 2-fold increase in expression levels over the other tissues. Equal loading of all the lanes was verified by filter hybridisation with a human GAPDH probe (data not shown).

Example 4

Expression of THP in Mammalian Cells

1. Expression of THP in 293 Cells

For expression of THP in mammalian cells 293 (transformed human, primary embryonic kidney cells), a plasmid bearing the relevant THP coding sequence is prepared, using vector pcDNA3.1 myc-his (Invitrogen). The plasmid contains nucleotides 17 through 3513 of SEQ ID NO:3. Vector pcDNA3.1 contains the c-myc epitope for detection of the recombinant protein with the anti-myc antibody, a C-terminal polyhistidine for purification with nickel chelate chromatography, and a Neomycin resistant gene for selection of stable transfectants. The forward primer for amplification of this THP cDNA is: 5'-AAGCGGCCGCATTATGGAAAGGATCATGTCGG GTCGCCGCT-3' (SEQ ID NO:8) which contains a 5' extension of 19 nucleotides to introduce the NotI cloning site and 22 nucleotides matching the THP sequence (nucleotides 17 through 38 of SEQ ID NO:3). The reverse primer is: 5'-AAGGATCCACCATACCTTCAGGCCT-3' (SEQ ID NO:9) which contains a 5' extension of 8 nucleotides to introduce an BamH1 restriction site for cloning and 17 nucleotides corresponding to the reverse complement of the THP sequence from bases 3497 to 3513 of SEQ ID NO:3. The PCR conditions are 55 C as the annealing temperature. The PCR product is gel purified and cloned into the NotI-BamH1 sites of the vector.

The DNA is purified using Qiagen chromatography columns and transfected into 293 cells using SUPERFACT transfection media (Qiagen). Transiently transfected cells are tested for expression after 24 hours of transfection, using western blots probed with antiHis and anti-THP peptide antibodies. Permanently transfected cells are selected with G418 and propagated. Production of the recombinant protein is detected from cells by Western blots probed with anti-His, anti-Myc or anti-THP peptide antibodies.

2. Expression of THP in COS Cells

For expression of the THP in COS7 cells, a polynucleotide molecule having the sequence given as nucleotides 17 through 3513 of SEQ ID NO:3 was cloned into vector pSecTag2A. Vector pSecTag2A contains the murine IgK chain leader sequence for secretion, the c-myc epitope for detection of the recombinant protein with the anti-myc antibody, a C-terminal polyhistidine for purification with nickel chelate chromatography, and a Zeocin resistant gene for selection of stable transfectants.

The forward primer is 5'-AAAAGCTTTATGGAAAGGATCATGTCGGGT CGCCGCTGC-3' (SEQ ID NO: 10). The first 15 nucleotides of this primer constitute a 5' extension which introduces an HindIII restriction site for cloning, followed by 22 nucleotides which correspond to nucleotide residues 17–38 of the sequence given in SEQ ID NO:3. The reverse primer is SEQ ID NO:9. This primer contains a 5'- extension of 8 nucleotides which introduces a BamH1 cloning site followed by 17 nucleotides which correspond to the reverse complement of bases 3497 to 3513 of the sequence given in SEQ ID NO:3.

The PCR consists of an initial denaturation step of 5 min at 95 C, 30 cycles of 30 sec denaturation at 95 C, 30 sec annealing at 58 C and 30 sec extension at 72 C, followed by 5 min extension at 72 C. The PCR product is gel purified and ligated into the XbaI and SalI sites of vector p3-CI. This construct is transformed into E. coli cells for amplification and DNA purification. The DNA is purified with Qiagen chromatography columns and transfected into COS 7 cells using Lipofectamine reagent from BRL, following the manufacturer's protocols. Forty eight and 72 hours after transfection, the media and the cells are tested for recombinant protein expression.

THP expressed from a COS cell culture can be purified by concentrating the cell-growth media to about 10 mg of protein/ml, and purifying the protein by, for example, chromatography. Purified THP is concentrated to 0.5 mg/ml in an Amicon concentrator fitted with a YM-10 membrane and stored at −80 C.

Example 5

Expression of THP in Insect Cells

For expression of THP in a baculovirus system, a polynucleotide molecule having the sequence given as nucleotides 17 through 3513 of SEQ ID NO:3 was amplified by PCR. The forward primer is SEQ ID NO:8. The first 19 nucleotides of this primer constitute a 5' extension which adds the NotI cloning site, followed by followed by 22 nucleotides which correspond to nucleotide residues 17 through 38 of the sequence given in SEQ ID NO:3. The reverse primer is SEQ ID NO:9. The first 8 nucleotides of this primer constitute a 5' extension which introduces the BamH1 cloning site, followed by followed by 17 nucleotides which correspond to the reverse complement of nucleotide residues 3497 through 3513 of the sequence given in SEQ ID NO:3.

The PCR product is gel purified, digested with NdeI and KpnI, and cloned into the corresponding sites of vector pACHTL-A (Pharningen, San Diego, Calif.). The pAcHTL expression vector contains the strong polyhedrin promoter of the Autographa californica nuclear polyhedrosis virus (AcMNPV), and a 6XHis tag upstream from the multiple cloning site. A protein kinase site for phosphorylation and a thrombin site for excision of the recombinant protein precede the multiple cloning site is also present. Of course, many other baculovirus vectors could be used in place of pAcHTL-A, such as pAc373, pVL941 and pAcIM1. Other suitable vectors for the expression of THP polypeptides can be used, provided that the vector construct includes appropriately located signals for transcription, translation, and trafficking, such as an in-frame AUG and a signal peptide, as required. Such vectors are described in Luckow et al., Virology 170:31–39, among others.

The virus is grown and isolated using standard baculovirus expression methods, such as those described in Summers et al. (A Manual of Methods for Baculovirus Vectors and Insect Cell Culture Procedures, Texas Agricultural Experimental Station Bulletin No. 1555 (1987)).

In a preferred embodiment, pAcHLT-A containing the THP gene is introduced into baculovirus using the "BaculoGold" transfection kit (Pharmingen, San Diego, Calif.) using methods established by the manufacturer. Individual virus isolates are analyzed for protein production by radiolabeling infected cells with $^{35}$S-methionine at 24 hours post infection. Infected cells are harvested at 48 hours post infection, and the labeled proteins are visualized by SDS-PAGE. Viruses exhibiting high expression levels can be isolated and used for scaled up expression.

For expression of the THP polypeptide in a Sf9 cells, a polynucleotide molecule having the sequence given as nucleotides 17 through 3513 of SEQ ID NO:3 is amplified by PCR using the primers and methods described above for baculovirus expression. The THP cDNA is cloned into vector pAcHLT-A (Pharmingen) for expression in Sf9 insect. The insert is cloned into the NotI and BamH1 sites, after elimination of an internal NdeI site (using the same primers described above for expression in baculovirus). DNA is purified with Qiagen chromatography columns and expressed in Sf9 cells. Preliminary Western blot experiments from non purified plaques are tested for the presence of the recombinant protein of the expected size which reacted with the THP-specific antibody. These results are confirmed after further purification and expression optimization in HiG5 cells.

Example 6

Interaction Trap/Two-Hybrid System

In order to assay for THP-interacting proteins, the interaction trap/two-hybrid library screening method can be used. This assay was first described in Fields, et al., Nature, 1989, 340, 245, which is incorporated herein by reference in its entirety. A protocol is published in Current Protocols in Molecular Biology 1999, John Wiley & Sons, NY and Ausubel, F. M. et al. 1992, Short protocols in molecular biology, fourth edition, Greene and Wiley-interscience, NY, which is incorporated herein by reference in its entirety. Kits are available from Clontech, Palo Alto, Calif. (Matchmaker Two-Hybrid System 3).

A fusion of the nucleotide sequences encoding all or partial THP and the yeast transcription factor GAL4 DNA-binding domain (DNA-BD) is constructed in an appropriate plasmid (ie. pGBKT7) using standard subcloning techniques. Similarly, a GAL4 active domain (AD) fusion library is constructed in a second plasmid (ie. pGADT7) from cDNA of potential THP-binding proteins (for protocols on forming cDNA libraries, see Sambrook et al. 1989, Molecular cloning: a laboratory manual, second edition, Cold Spring Harbor Press, Cold Spring Harbor, N.Y.), which is incorporated herein by reference in its entirety. The DNA-BD/THP fusion construct is verified by sequencing, and tested for autonomous reporter gene activation and cell toxicity, both of which would prevent a successful two-hybrid analysis. Similar controls are performed with the AD/library fusion construct to ensure expression in host cells and lack of transcriptional activity. Yeast cells are transformed (ca. $10^5$ transformants/mg DNA) with both the THP and library fusion plasmids according to standard procedure (Ausubel, et al., 1992, *Short protocols in molecular biology*, fourth edition, Greene and Wiley-interscience, NY, which is incorporated herein by reference in its entirety). In vivo binding of DNA-BD/THP with AD/library proteins results in transcription of specific yeast plasmid reporter genes (ie. lacZ, HIS3, ADE2, LEU2). Yeast cells are plated on nutrient-deficient media to screen for expression of reporter genes. Colonies are dually assayed for β-galactosidase activity upon growth in Xgal (5-bromo-4-chloro-3-indolyl-β-D-galactoside) supplemented media (filter assay for β-galactosidase activity is described in Breeden, et al., *Cold Spring Harb. Symp. Quant. Biol.*, 1985, 50, 643, which is incorporated herein by reference in its entirety). Positive AD-library plasmids are rescued from transformants and reintroduced into the original yeast strain as well as other strains containing unrelated DNA-BD fusion proteins to confirm specific THP/library protein interactions. Insert DNA is sequenced to verify the presence of an open reading frame fused to GAL4 AD and to determine the identity of the THP-binding protein.

Example 7

Mobility Shift DNA-Binding Assay Using Gel Eelectrophoresis

A gel electrophoresis mobility shift assay can rapidly detect specific protein-DNA interactions. Protocols are widely available in such manuals as Sambrook et al. 1989, *Molecular cloning: a laboratory manual*, second edition, Cold Spring Harbor Press, Cold Spring Harbor, N.Y. and Ausubel, F. M. et al. 1992, *Short protocols in molecular biology*, fourth edition, Greene and Wiley-interscience, NY, each of which is incorporated herein by reference in its entirety.

Probe DNA(<300 bp) is obtained from synthetic oligonucleotides, restriction endonuclease fragments, or PCR fragments and end-labeled with $^{32}$p. An aliquot of purified THP (ca. 15 μg) or crude THP extract (ca. 15 ng) is incubated at constant temperature (in the range 22–37 C) for at least 30 minutes in 10–15 μl of buffer (i.e., TAE or TBE, pH 8.0–8.5) containing radiolabeled probe DNA, nonspecific carrier DNA (ca. 1 μg), BSA (300 μg/ml), and 10% (v/v) glycerol. The reaction mixture is then loaded onto a polyacrylamide gel and run at 30–35 mA until good separation of free probe DNA from protein-DNA complexes occurs. The gel is then dried and bands corresponding to free DNA and protein-DNA complexes are detected by autoradiography.

Example 8

Assay to Identify Compounds that Modulate THP Activity

THP is capable of auto-poly[ADP]-ribosylation through the activity of the PARP domain. To screen for this THP activity, THP expressed in baculovirus is used (see, Example 5). Four μg of THP is incubated in 100 μl of assay buffer (50 mM Tris, pH 8.0, 4 mM $MgCl_2$, 0.2 mM DTT) together with 1.3 μM $^{32}$P-labeled $NAD^+$, at 25 C for 30 minutes. Incorporation of $^{32}$P-labeled $NAD^+$ is measured by TCA precipitation, by addition of 20% TCA, and collection by filtration of insoluble material onto glass filters. The filters are counted by scintillation counting in a fluid beta-counter, and the resulting counts are used as a measure for THP PARP activity. This same assay can also be used, for example, to screen large libraries of chemical compounds for small molecules that are THP PARP inhibitors.

Some of the preferred embodiments of the invention described above are outlined below and include, but are not limited to, the following embodiments. As those skilled in the art will appreciate, numerous changes and modifications may be made to the preferred embodiments of the invention without departing from the spirit of the invention. It is intended that all such variations fall within the scope of the invention. The entire disclosure of each publication cited herein is hereby incorporated by reference.

What is claimed is:

1. An isolated nucleic acid molecule comprising a nucleotide sequence selected from the group consisting of:
   a) SEQ ID NO:3;
   b) SEQ ID NO:4; and
   c) a sequence that encodes a polypeptide comprising SEQ ID NO:5;
   said nucleic acid molecule encoding at least a portion of a tankyrase homolog protein.

2. The nucleic acid molecule of claim 1 wherein said nucleic acid molecule is DNA.

3. The nucleic acid molecule of claim 1 wherein said nucleic acid molecule is RNA.

4. An isolated nucleic acid molecule comprising SEQ ID NO:4.

5. An expression vector comprising a nucleic acid molecule of claim 1.

6. An expression vector comprising the nucleic acid molecule of claim 4.

7. The vector of claim 5 wherein said vector is a plasmid.

8. The vector of claim 5 wherein said vector is a viral particle.

9. The vector of claim 8 wherein said vector is selected from the group consisting of adenoviruses, parvoviruses, herpesviruses, poxviruses, adeno-associated viruses, Semliki Forest viruses, vaccinia viruses, and retroviruses.

10. The vector of claim 5 wherein said nucleic acid molecule is operably connected to a promoter selected from the group consisting of simian virus 40, mouse mammary tumor virus, long terminal repeat of human immunodeficiency virus, maloney virus, cytomegalovirus immediate early promoter, Epstein Barr virus, rous sarcoma virus, human actin, human myosin, human hemoglobin, human muscle creatine kinase, and human metallothionein.

11. A host cell transformed with a vector of claim 5.

12. The transformed host cell of claim 11 wherein said cell is a bacterial cell.

13. The transformed host cell of claim 12 wherein said bacterial cell is *E. coli*.

14. The transformed host cell of claim 11 wherein said cell is a yeast.

15. The transformed host cell of claim 14 wherein said yeast is *S. cerevisiae*.

16. The transformed host cell of claim 11 wherein said cell is an insect cell.

17. The transformed host cell of claim 16 wherein said insect cell is *S. frugiperda*.

18. The transformed host cell of claim 11 wherein said cell is a mammalian cell.

19. The transformed host cell of claim 18 wherein mammalian cell is selected from the group consisting of chinese hamster ovary cells, HeLa cells, African green monkey kidney cells, human 293 cells, and murine 3T3 fibroblasts.

20. A method of producing a polypeptide comprising SEQ ID NO:5 comprising the steps of:
    a) introducing a recombinant expression vector of claim 5 into a compatible host cell;
    b) growing said host cell under conditions for expression of said polypeptide; and
    c) recovering said polypeptide.

21. The method of claim 20 wherein said host cell is lysed and said polypeptide is recovered from the lysate of said host cell.

22. The method of claim 20 wherein said polypeptide is recovered by purifying the culture medium without lysing said host cell.

23. A composition comprising a nucleic acid molecule of claim 1 and an acceptable carrier or diluent.

24. A composition comprising a recombinant expression vector of claim 5 and an acceptable carrier or diluent.

25. A kit comprising a nucleic acid molecule of claim 1.

26. The kit of claim 25 further comprising an additional kit component.

27. The kit of claim 26 wherein said additional kit component comprises instructions.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial
<220> FEATURE:
<223> OTHER INFORMATION: PCR Primers

<400> SEQUENCE: 1
gagtatttgt tacaacacgg         20

<210> SEQ ID NO 2
<211> LENGTH: 18
<212> TYPE: DNA
<213> ORGANISM: Artificial
<220> FEATURE:
<223> OTHER INFORMATION: PCR Primers

<400> SEQUENCE: 2
aatctccttc agctcctt         18

<210> SEQ ID NO 3
<211> LENGTH: 4512
<212> TYPE: DNA
<213> ORGANISM: Artificial
<220> FEATURE:
<223> OTHER INFORMATION: PCR Primers
<221> NAME/KEY: misc_feature
<222> LOCATION: (1124)..(1124)
<223> OTHER INFORMATION: n is any nucleic acid
<221> NAME/KEY: misc_feature
<222> LOCATION: (2672)..(2672)
<223> OTHER INFORMATION: n is any nucleic acid

<400> SEQUENCE: 3

| | | | | | |
|---|---|---|---|---|---|
| gaattccgcg | gcggccagga | tcatgtcggg | tcgccgctgc | gccggcgggg | gagcggcctg | 60 |
| cgcgagcgcc | gcggccgagg | ccgtggagcc | ggccgcccga | gagctgttcg | aggcgtgccg | 120 |
| caacggggac | gtggaacgag | tcaagaggct | ggtgacgcct | gagaaggtga | acagccgcga | 180 |
| cacggcgggc | aggaaatcca | ccccgctgca | cctcgccgca | ggttttgggc | ggaaagacgt | 240 |
| agttgaatat | ttgcttcaga | atggtgcaaa | tgtccaagca | cgtgatgatg | ggggccttat | 300 |
| tcctcttcat | aatgcatgct | cttttggtca | tgctgaagta | gtcaatctcc | ttttgcgaca | 360 |
| tggtgcagac | cccaatgctc | gagataattg | gaattatact | cctctccatg | aagctgcaat | 420 |
| taaaggaaag | attgatgttt | gcattgtgct | gttacagcat | ggagctgagc | caaccatccg | 480 |
| aaatacagat | ggaaggacag | cattggattt | agcagatcca | tctgccaaag | cagtgcttac | 540 |
| tggtgaatat | aagaaagatg | aactcttaga | aagtgccagg | agtggcaatg | aagaaaaaat | 600 |
| gatggctcta | ctcacaccat | taaatgtcaa | ctgccacgca | agtgatggca | gaaagtcaac | 660 |
| tccattacat | ttggcagcag | gatataacag | agtaaagatt | gtacagctgt | tactgcaaca | 720 |
| tggagctgat | gtccatgcta | aagataaagg | tgatctggta | ccattacaca | atgcctgttc | 780 |
| ttatggtcat | tatgaagtaa | ctgaactttt | ggtcaagcat | ggtgcctgtg | taaatgcaat | 840 |
| ggacttgtgg | caattcactc | ctcttcatga | ggcagcttct | aagaacaggg | ttgaagtatg | 900 |
| ttctcttctc | ttaagttatg | gtgcagaccc | aacactgctc | aattgtcaca | ataaaagtgc | 960 |
| tatagacttg | gctcccacac | cacagttaaa | agaaagatta | gcatatgaat | taaaggcca | 1020 |
| ctcgttgctg | caagctgcac | gagaagctga | tgttactcga | atcaaaaaac | atctctctct | 1080 |
| ggaaatggtg | aatttcaagc | atcctcaaac | acatgaaaca | gcantgcatt | gtgctgctgc | 1140 |
| atctccatat | cccaaaagaa | agcaaatatg | tgaactgttg | ctaagaaaag | gagcaamcat | 1200 |
| caatgaaaag | actaaagaat | tcttgactcc | tctgcacgtg | gcatctgaga | aagctcataa | 1260 |
| tgatrttgtt | gaagtagtgg | tgaaacatga | agcaaaggtt | aatgctctgg | ataatcttgg | 1320 |
| tcagacttct | ctacacagag | ctgcatattg | tggtcatcta | caaacctgcc | gcctactcct | 1380 |
| gagctatggg | tgtgatccta | acattatatc | ccttcagggc | tttactgctt | acagatggg | 1440 |
| aaatgaaaat | gtacagcaac | tcctccaaga | gggtatctca | ttaggtaatt | cagaggcaga | 1500 |
| cagacaattg | ctggaagctg | caaaggctgg | agatgtcgaa | actgtaaaaa | aactgtgtac | 1560 |
| tgttcagagt | gtcaactgca | gagacattga | agggcgtcag | tctacaccac | ttcattttgc | 1620 |
| agctgggtat | aacagagtgt | ccgtggtgga | atatctgcta | cagcatggag | ctgatgtgca | 1680 |
| tgctaaagat | aaagrrgscc | ttgtacccttt | gcacaatgca | tgttcttatg | gacattatga | 1740 |
| agttgcagaa | cttcttgtta | aacatggagc | agtagttaat | gtagctgatt | tatggaaatt | 1800 |
| tacacccttta | catgaagcag | cagcaaaagg | aaaatatgaa | atttgcaaac | ttctgctcca | 1860 |

-continued

```
gcatggtgca gaccctacaa aaaaaaacag ggatggaaat actcctttgg atcttgttaa   1920
agatggagat acagatattc aagatctgct tagggagat gcagctttgc tagatgctgc    1980
caagaagagt tgtttagcca gagtgaagaa gttgtcttct cctgataatg taaattgccg   2040
cgatacccaa ggcagacatt caacaccttt acatttagca gctggttata ataatttaga   2100
agttgcagag tatttgttac aacacggagc tgatgtgaat gcccaagaca aaggaggact   2160 tattcctttta cataatgcag catcttacgg gcatgtagat gtagcagctc tactaataaa   2220
gtataatgca tgtgtcaatg ccacggacaa atgggctttc acacctttgc acgaagcagc   2280
ccaaaaggga cgaacacagc tttgtgcttt gktgctagcc catggagctg acccgactct   2340
taaaaatcag gaaggacaaa cacctttaga tttagtttca gcggatgatg tcagcgctct   2400
tctgacagca gccatgcccc catctgctct gccctcttgt tacaagcctc aagtgctcaa   2460
tggtgtgaga agcccaggag ccactgcaga tgctctctct tcaggtccat ctagcccatc   2520
aagcctttct gcagccagca gtcttgacaa cttatctggg agtttttcag aactgtcttc   2580
agtagttagt tcaagtggaa cagagggtgc ttccagtttg gagaaaaagg aggttccagg   2640
agtagatttt agcataactc aattcgtaag gnatcttgga cttgagcacc taatggatat   2700
atttgagaga gaacagatca ctttggatgt attagttgag atggggcaca aggagctgaa   2760
ggagattgga atcaatgctt atggacatag gcacaaacta attaaaggag tcgagagact   2820
tatctccgga caacaaggtc ttaacccata tttaactttg aacacctctg gtagtggaac   2880
aattcttata gatctgtctc ctgatgataa agagtttcag tctgtggagg aagagatgca   2940
aagtacagtt cgagagcaca gagatggagg tcatgcaggt ggaatcttca acagatacaa   3000
tattctcaag attcagaagg tttgtaacaa gaaactatgg gaaagataca ctcaccggag   3060
aaaagaagtt tctgaagaaa accacaacca tgccaatgaa cgaatgctat ttcatgggtc   3120
tccttttgtg aatgcaatta ccacaaagg ctttgatgaa aggcatgcgt acataggtgg   3180
tatgtttgga gctggcattt attttgctga aaactcttcc aaaagcaatc aatatgtata   3240
tggaattgga ggaggtactg ggtgtccagt tcacaaagac agatcttgtt acatttgcca   3300
caggcagctg ctcttttgcc gggtaacctt gggaaagtct ttcctgcagt tcagtgcaat   3360
gaaaatggca cattctcctc caggtcatca ctcagtcact ggtaggccca gtgtaaatgg   3420
cctagcatta gctgaatatg ttatttacag aggagaacag gcttatcctg agtatttaat   3480
tacttaccag attatgaggc ctgaaggtat ggtcgatgga taaatagtta ttttaagaaa   3540
ctaattccac tgaacctaaa atcatcaaag cagcagtggc ctctacgttt tactcctttg   3600
ctgaaaaaaa atcatcttgc ccacaggcct gtggcaaaag gataaaaatg tgaacgaagt   3660
ttaacattct gacttgataa agctttaata atgtacagtg ttttctaaat atttcctgtt   3720
ttttcagcac tttaacagat gccattccag gttaaactgg gttgtctgta ctaaattata   3780
aacagagtta acttgaacct tttatatgtt atgcattgat tctaacaaac tgtaatgccc   3840
tcaacagaac taatttttact aatacaatac tgtgttcttt aaaacacagc atttacactg   3900
aatacaattt catttgtaaa actgtaaata agagcttttg tactagccca gtatttattt   3960
acattgcttt gtaatataaa tctgttttag aactgcagcg gtttacaaaa tttttttcata   4020 tgtattgttc atctatactt gcatcttaca tcgtcatgat tgagtgatct ttacatttga   4080
ttccagaggc tatgttcagt tgttagttgg gaaagattga gttatcagat ttaatttgcc   4140
gatgggagcc tttatctgtc attagaaatc tttctcattt aagaacttat gaatatgctg   4200
aagatttaat ttgtgatacc tttgtatgta tgagacacat tccaaagaac tctaactatg   4260
```

-continued

```
ataggtcctg attactaaag aagcttcttt actggcctca atttctagct ttcatgttgg      4320
aaaattttct gcagtccttc tgtgaaaatt agagcaaagt gctcctgttt tttagagaaa      4380
ctaaatcttg ctgttgaaca attattgtgt tcttttcatg aacataagt aggatgttac      4440 atttccaggg tgggaagggt aatcctaaat catttcccaa tctattctaa ttaccttaaa      4500
tctaaagggg aa                                                         4512
```

<210> SEQ ID NO 4
<211> LENGTH: 3498
<212> TYPE: DNA
<213> ORGANISM: Artificial
<220> FEATURE:
<223> OTHER INFORMATION: PCR Primers
<221> NAME/KEY: CDS
<222> LOCATION: (1)..(3498)
<221> NAME/KEY: misc_feature
<223> OTHER INFORMATION: Xaa is any amino acid
<221> NAME/KEY: misc_feature
<222> LOCATION: (1102)..(1102)
<223> OTHER INFORMATION: n is any nucleic acid
<221> NAME/KEY: misc_feature
<222> LOCATION: (2650)..(2650)
<223> OTHER INFORMATION: n is any nucleic acid

<400> SEQUENCE: 4

```
atg tcg ggt cgc cgc tgc gcc ggc ggg gga gcg gcc tgc gcg agc gcc       48
Met Ser Gly Arg Arg Cys Ala Gly Gly Gly Ala Ala Cys Ala Ser Ala
1               5                   10                  15 gcg gcc gag gcc gtg gag ccg gcc gcc cga gag ctg ttc gag gcg tgc       96
Ala Ala Glu Ala Val Glu Pro Ala Ala Arg Glu Leu Phe Glu Ala Cys
            20                  25                  30 cgc aac ggg gac gtg gaa cga gtc aag agg ctg gtg acg cct gag aag      144
Arg Asn Gly Asp Val Glu Arg Val Lys Arg Leu Val Thr Pro Glu Lys
        35                  40                  45 gtg aac agc cgc gac acg gcg ggc agg aaa tcc acc ccg ctg cac ctc      192
Val Asn Ser Arg Asp Thr Ala Gly Arg Lys Ser Thr Pro Leu His Leu
    50                  55                  60 gcc gca ggt ttt ggg cgg aaa gac gta gtt gaa tat ttg ctt cag aat      240
Ala Ala Gly Phe Gly Arg Lys Asp Val Val Glu Tyr Leu Leu Gln Asn
65                  70                  75                  80 ggt gca aat gtc caa gca cgt gat gat ggg ggc ctt att cct ctt cat      288
Gly Ala Asn Val Gln Ala Arg Asp Asp Gly Gly Leu Ile Pro Leu His
                85                  90                  95 aat gca tgc tct ttt ggt cat gct gaa gta gtc aat ctc ctt ttg cga      336
Asn Ala Cys Ser Phe Gly His Ala Glu Val Val Asn Leu Leu Leu Arg
            100                 105                 110 cat ggt gca gac ccc aat gct cga gat aat tgg aat tat act cct ctc      384
His Gly Ala Asp Pro Asn Ala Arg Asp Asn Trp Asn Tyr Thr Pro Leu
        115                 120                 125 cat gaa gct gca att aaa gga aag att gat gtt tgc att gtg ctg tta      432
His Glu Ala Ala Ile Lys Gly Lys Ile Asp Val Cys Ile Val Leu Leu
    130                 135                 140 cag cat gga gct gag cca acc atc cga aat aca gat gga agg aca gca      480
Gln His Gly Ala Glu Pro Thr Ile Arg Asn Thr Asp Gly Arg Thr Ala
145                 150                 155                 160 ttg gat tta gca gat cca tct gcc aaa gca gtg ctt act ggt gaa tat      528
Leu Asp Leu Ala Asp Pro Ser Ala Lys Ala Val Leu Thr Gly Glu Tyr
                165                 170                 175 aag aaa gat gaa ctc tta gaa agt gcc agg agt ggc aat gaa gaa aaa      576
Lys Lys Asp Glu Leu Leu Glu Ser Ala Arg Ser Gly Asn Glu Glu Lys
            180                 185                 190
```

```
                                            -continued atg atg gct cta ctc aca cca tta aat gtc aac tgc cac gca agt gat    624
Met Met Ala Leu Leu Thr Pro Leu Asn Val Asn Cys His Ala Ser Asp
            195                 200                 205 ggc aga aag tca act cca tta cat ttg gca gca gga tat aac aga gta    672
Gly Arg Lys Ser Thr Pro Leu His Leu Ala Ala Gly Tyr Asn Arg Val
210                 215                 220 aag att gta cag ctg tta ctg caa cat gga gct gat gtc cat gct aaa    720
Lys Ile Val Gln Leu Leu Leu Gln His Gly Ala Asp Val His Ala Lys
225                 230                 235                 240 gat aaa ggt gat ctg gta cca tta cac aat gcc tgt tct tat ggt cat    768
Asp Lys Gly Asp Leu Val Pro Leu His Asn Ala Cys Ser Tyr Gly His
            245                 250                 255 tat gaa gta act gaa ctt ttg gtc aag cat ggt gcc tgt gta aat gca    816
Tyr Glu Val Thr Glu Leu Leu Val Lys His Gly Ala Cys Val Asn Ala
            260                 265                 270 atg gac ttg tgg caa ttc act cct ctt cat gag gca gct tct aag aac    864
Met Asp Leu Trp Gln Phe Thr Pro Leu His Glu Ala Ala Ser Lys Asn
        275                 280                 285 agg gtt gaa gta tgt tct ctt ctc tta agt tat ggt gca gac cca aca    912
Arg Val Glu Val Cys Ser Leu Leu Leu Ser Tyr Gly Ala Asp Pro Thr
290                 295                 300 ctg ctc aat tgt cac aat aaa agt gct ata gac ttg gct ccc aca cca    960
Leu Leu Asn Cys His Asn Lys Ser Ala Ile Asp Leu Ala Pro Thr Pro
305                 310                 315                 320 cag tta aaa gaa aga tta gca tat gaa ttt aaa ggc cac tcg ttg ctg   1008
Gln Leu Lys Glu Arg Leu Ala Tyr Glu Phe Lys Gly His Ser Leu Leu
            325                 330                 335 caa gct gca cga gaa gct gat gtt act cga atc aaa aaa cat ctc tct   1056
Gln Ala Ala Arg Glu Ala Asp Val Thr Arg Ile Lys Lys His Leu Ser
            340                 345                 350 ctg gaa atg gtg aat ttc aag cat cct caa aca cat gaa aca gca ntg   1104
Leu Glu Met Val Asn Phe Lys His Pro Gln Thr His Glu Thr Ala Xaa
        355                 360                 365 cat tgt gct gct gca tct cca tat ccc aaa aga aag caa ata tgt gaa   1152
His Cys Ala Ala Ala Ser Pro Tyr Pro Lys Arg Lys Gln Ile Cys Glu
370                 375                 380 ctg ttg cta aga aaa gga gca amc atc aat gaa aag act aaa gaa ttc   1200
Leu Leu Leu Arg Lys Gly Ala Xaa Ile Asn Glu Lys Thr Lys Glu Phe
385                 390                 395                 400 ttg act cct ctg cac gtg gca tct gag aaa gct cat aat gat rtt gtt   1248
Leu Thr Pro Leu His Val Ala Ser Glu Lys Ala His Asn Asp Xaa Val
            405                 410                 415 gaa gta gtg gtg aaa cat gaa gca aag gtt aat gct ctg gat aat ctt   1296
Glu Val Val Val Lys His Glu Ala Lys Val Asn Ala Leu Asp Asn Leu
            420                 425                 430 ggt cag act tct cta cac aga gct gca tat tgt ggt cat cta caa acc   1344
Gly Gln Thr Ser Leu His Arg Ala Ala Tyr Cys Gly His Leu Gln Thr
        435                 440                 445 tgc cgc cta ctc ctg agc tat ggg tgt gat cct aac att ata tcc ctt   1392
Cys Arg Leu Leu Leu Ser Tyr Gly Cys Asp Pro Asn Ile Ile Ser Leu
450                 455                 460 cag ggc ttt act gct tta cag atg gga aat gaa aat gta cag caa ctc   1440
Gln Gly Phe Thr Ala Leu Gln Met Gly Asn Glu Asn Val Gln Gln Leu
465                 470                 475                 480 ctc caa gag ggt atc tca tta ggt aat tca gag gca gac aga caa ttg   1488
Leu Gln Glu Gly Ile Ser Leu Gly Asn Ser Glu Ala Asp Arg Gln Leu
            485                 490                 495 ctg gaa gct gca aag gct gga gat gtc gaa act gta aaa aaa ctg tgt   1536
Leu Glu Ala Ala Lys Ala Gly Asp Val Glu Thr Val Lys Lys Leu Cys
        500                 505                 510
```

```
act gtt cag agt gtc aac tgc aga gac att gaa ggg cgt cag tct aca         1584
Thr Val Gln Ser Val Asn Cys Arg Asp Ile Glu Gly Arg Gln Ser Thr
            515                 520                 525 cca ctt cat ttt gca gct ggg tat aac aga gtg tcc gtg gtg gaa tat         1632
Pro Leu His Phe Ala Ala Gly Tyr Asn Arg Val Ser Val Val Glu Tyr
        530                 535                 540 ctg cta cag cat gga gct gat gtg cat gct aaa gat aaa grr gsc ctt         1680
Leu Leu Gln His Gly Ala Asp Val His Ala Lys Asp Lys Xaa Xaa Leu
545                 550                 555                 560 gta cct ttg cac aat gca tgt tct tat gga cat tat gaa gtt gca gaa         1728
Val Pro Leu His Asn Ala Cys Ser Tyr Gly His Tyr Glu Val Ala Glu
                565                 570                 575 ctt ctt gtt aaa cat gga gca gta gtt aat gta gct gat tta tgg aaa         1776
Leu Leu Val Lys His Gly Ala Val Val Asn Val Ala Asp Leu Trp Lys
            580                 585                 590 ttt aca cct tta cat gaa gca gca gca aaa gga aaa tat gaa att tgc         1824
Phe Thr Pro Leu His Glu Ala Ala Ala Lys Gly Lys Tyr Glu Ile Cys
        595                 600                 605 aaa ctt ctg ctc cag cat ggt gca gac cct aca aaa aaa aac agg gat         1872
Lys Leu Leu Leu Gln His Gly Ala Asp Pro Thr Lys Lys Asn Arg Asp
610                 615                 620 gga aat act cct ttg gat ctt gtt aaa gat gga gat aca gat att caa         1920
Gly Asn Thr Pro Leu Asp Leu Val Lys Asp Gly Asp Thr Asp Ile Gln
                625                 630                 635                 640 gat ctg ctt agg gga gat gca gct ttg cta gat gct gcc aag aag agt         1968
Asp Leu Leu Arg Gly Asp Ala Ala Leu Leu Asp Ala Ala Lys Lys Ser
                    645                 650                 655 tgt tta gcc aga gtg aag aag ttg tct tct cct gat aat gta aat tgc         2016
Cys Leu Ala Arg Val Lys Lys Leu Ser Ser Pro Asp Asn Val Asn Cys
                660                 665                 670 cgc gat acc caa ggc aga cat tca aca cct tta cat tta gca gct ggt         2064
Arg Asp Thr Gln Gly Arg His Ser Thr Pro Leu His Leu Ala Ala Gly
            675                 680                 685 tat aat aat tta gaa gtt gca gag tat ttg tta caa cac gga gct gat         2112
Tyr Asn Asn Leu Glu Val Ala Glu Tyr Leu Leu Gln His Gly Ala Asp
        690                 695                 700 gtg aat gcc caa gac aaa gga gga ctt att cct tta cat aat gca gca         2160
Val Asn Ala Gln Asp Lys Gly Gly Leu Ile Pro Leu His Asn Ala Ala
705                 710                 715                 720 tct tac ggg cat gta gat gta gca gct cta cta ata aag tat aat gca         2208
Ser Tyr Gly His Val Asp Val Ala Ala Leu Leu Ile Lys Tyr Asn Ala
                725                 730                 735 tgt gtc aat gcc acg gac aaa tgg gct ttc aca cct ttg cac gaa gca         2256
Cys Val Asn Ala Thr Asp Lys Trp Ala Phe Thr Pro Leu His Glu Ala
                740                 745                 750 gcc caa aag gga cga aca cag ctt tgt gct ttg ktg cta gcc cat gga         2304
Ala Gln Lys Gly Arg Thr Gln Leu Cys Ala Leu Xaa Leu Ala His Gly
            755                 760                 765 gct gac ccg act ctt aaa aat cag gaa gga caa aca cct tta gat tta         2352
Ala Asp Pro Thr Leu Lys Asn Gln Glu Gly Gln Thr Pro Leu Asp Leu
        770                 775                 780 gtt tca gcg gat gat gtc agc gct ctt ctg aca gca gcc atg ccc cca         2400
Val Ser Ala Asp Asp Val Ser Ala Leu Leu Thr Ala Ala Met Pro Pro
785                 790                 795                 800 tct gct ctg ccc tct tgt tac aag cct caa gtg ctc aat ggt gtg aga         2448
Ser Ala Leu Pro Ser Cys Tyr Lys Pro Gln Val Leu Asn Gly Val Arg
                805                 810                 815 agc cca gga gcc act gca gat gct ctc tct tca ggt cca tct agc cca         2496
Ser Pro Gly Ala Thr Ala Asp Ala Leu Ser Ser Gly Pro Ser Ser Pro
```

-continued

```
                820                 825                 830
tca agc ctt tct gca gcc agc agt ctt gac aac tta tct ggg agt ttt       2544
Ser Ser Leu Ser Ala Ala Ser Ser Leu Asp Asn Leu Ser Gly Ser Phe
        835                 840                 845 tca gaa ctg tct tca gta gtt agt tca agt gga aca gag ggt gct tcc       2592
Ser Glu Leu Ser Ser Val Val Ser Ser Gly Thr Glu Gly Ala Ser
850                 855                 860 agt ttg gag aaa aag gag gtt cca gga gta gat ttt agc ata act caa       2640
Ser Leu Glu Lys Lys Glu Val Pro Gly Val Asp Phe Ser Ile Thr Gln
865                 870                 875                 880 ttc gta agg nat ctt gga ctt gag cac cta atg gat ata ttt gag aga       2688
Phe Val Arg Xaa Leu Gly Leu Glu His Leu Met Asp Ile Phe Glu Arg
                885                 890                 895 gaa cag atc act ttg gat gta tta gtt gag atg ggg cac aag gag ctg       2736
Glu Gln Ile Thr Leu Asp Val Leu Val Glu Met Gly His Lys Glu Leu
        900                 905                 910 aag gag att gga atc aat gct tat gga cat agg cac aaa cta att aaa       2784
Lys Glu Ile Gly Ile Asn Ala Tyr Gly His Arg His Lys Leu Ile Lys
        915                 920                 925 gga gtc gag aga ctt atc tcc gga caa caa ggt ctt aac cca tat tta       2832
Gly Val Glu Arg Leu Ile Ser Gly Gln Gln Gly Leu Asn Pro Tyr Leu
930                 935                 940 act ttg aac acc tct ggt agt gga aca att ctt ata gat ctg tct cct       2880
Thr Leu Asn Thr Ser Gly Ser Gly Thr Ile Leu Ile Asp Leu Ser Pro
945                 950                 955                 960 gat gat aaa gag ttt cag tct gtg gag gaa gag atg caa agt aca gtt       2928
Asp Asp Lys Glu Phe Gln Ser Val Glu Glu Glu Met Gln Ser Thr Val
                965                 970                 975 cga gag cac aga gat gga ggt cat gca ggt gga atc ttc aac aga tac       2976
Arg Glu His Arg Asp Gly Gly His Ala Gly Gly Ile Phe Asn Arg Tyr
        980                 985                 990 aat att ctc aag att cag aag gtt tgt aac aag aaa cta tgg gaa aga       3024
Asn Ile Leu Lys Ile Gln Lys Val Cys Asn Lys Lys Leu Trp Glu Arg
        995                 1000                1005 tac act cac cgg aga aaa gaa gtt tct gaa gaa aac cac aac cat          3069
Tyr Thr His Arg Arg Lys Glu Val Ser Glu Glu Asn His Asn His
        1010                1015                1020 gcc aat gaa cga atg cta ttt cat ggg tct cct ttt gtg aat gca          3114
Ala Asn Glu Arg Met Leu Phe His Gly Ser Pro Phe Val Asn Ala
        1025                1030                1035 att atc cac aaa ggc ttt gat gaa agg cat gcg tac ata ggt ggt          3159
Ile Ile His Lys Gly Phe Asp Glu Arg His Ala Tyr Ile Gly Gly
        1040                1045                1050 atg ttt gga gct ggc att tat ttt gct gaa aac tct tcc aaa agc          3204
Met Phe Gly Ala Gly Ile Tyr Phe Ala Glu Asn Ser Ser Lys Ser
        1055                1060                1065 aat caa tat gta tat gga att gga gga ggt act ggg tgt cca gtt          3249
Asn Gln Tyr Val Tyr Gly Ile Gly Gly Gly Thr Gly Cys Pro Val
        1070                1075                1080 cac aaa gac aga tct tgt tac att tgc cac agg cag ctg ctc ttt          3294
His Lys Asp Arg Ser Cys Tyr Ile Cys His Arg Gln Leu Leu Phe
        1085                1090                1095 tgc cgg gta acc ttg gga aag tct ttc ctg cag ttc agt gca atg          3339
Cys Arg Val Thr Leu Gly Lys Ser Phe Leu Gln Phe Ser Ala Met
        1100                1105                1110 aaa atg gca cat tct cct cca ggt cat cac tca gtc act ggt agg          3384
Lys Met Ala His Ser Pro Pro Gly His His Ser Val Thr Gly Arg
        1115                1120                1125 ccc agt gta aat ggc cta gca tta gct gaa tat gtt att tac aga          3429
```

```
Pro Ser Val Asn Gly Leu Ala Leu Ala Glu Tyr Val Ile Tyr Arg
    1130                1135                1140 gga gaa cag gct tat cct gag tat tta att act tac cag att atg      3474
Gly Glu Gln Ala Tyr Pro Glu Tyr Leu Ile Thr Tyr Gln Ile Met
    1145                1150                1155 agg cct gaa ggt atg gtc gat gga                                  3498
Arg Pro Glu Gly Met Val Asp Gly
    1160                1165

<210> SEQ ID NO 5
<211> LENGTH: 1166
<212> TYPE: PRT
<213> ORGANISM: Artificial
<220> FEATURE:
<221> NAME/KEY: misc_feature
<223> OTHER INFORMATION: Xaa is any amino acid
<221> NAME/KEY: misc_feature
<222> LOCATION: (1102)..(1102)
<223> OTHER INFORMATION: n is any nucleic acid
<221> NAME/KEY: misc_feature
<222> LOCATION: (2650)..(2650)
<223> OTHER INFORMATION: n is any nucleic acid

<400> SEQUENCE: 5

Met Ser Gly Arg Arg Cys Ala Gly Gly Ala Ala Cys Ala Ser Ala
1               5                   10                  15

Ala Ala Glu Ala Val Glu Pro Ala Ala Arg Glu Leu Phe Glu Ala Cys
                20                  25                  30

Arg Asn Gly Asp Val Glu Arg Val Lys Arg Leu Val Thr Pro Glu Lys
            35                  40                  45

Val Asn Ser Arg Asp Thr Ala Gly Arg Lys Ser Thr Pro Leu His Leu
    50                  55                  60

Ala Ala Gly Phe Gly Arg Lys Asp Val Val Glu Tyr Leu Leu Gln Asn
65                  70                  75                  80

Gly Ala Asn Val Gln Ala Arg Asp Asp Gly Gly Leu Ile Pro Leu His
                85                  90                  95

Asn Ala Cys Ser Phe Gly His Ala Glu Val Val Asn Leu Leu Leu Arg
            100                 105                 110

His Gly Ala Asp Pro Asn Ala Arg Asp Asn Trp Asn Tyr Thr Pro Leu
        115                 120                 125

His Glu Ala Ala Ile Lys Gly Lys Ile Asp Val Cys Ile Val Leu Leu
    130                 135                 140

Gln His Gly Ala Glu Pro Thr Ile Arg Asn Thr Asp Gly Arg Thr Ala
145                 150                 155                 160

Leu Asp Leu Ala Asp Pro Ser Ala Lys Ala Val Leu Thr Gly Glu Tyr
                165                 170                 175

Lys Lys Asp Glu Leu Leu Glu Ser Ala Arg Ser Gly Asn Glu Glu Lys
            180                 185                 190

Met Met Ala Leu Leu Thr Pro Leu Asn Val Asn Cys His Ala Ser Asp
        195                 200                 205

Gly Arg Lys Ser Thr Pro Leu His Leu Ala Ala Gly Tyr Asn Arg Val
    210                 215                 220

Lys Ile Val Gln Leu Leu Leu Gln His Gly Ala Asp Val His Ala Lys
225                 230                 235                 240

Asp Lys Gly Asp Leu Val Pro Leu His Asn Ala Cys Ser Tyr Gly His
                245                 250                 255

Tyr Glu Val Thr Glu Leu Leu Val Lys His Gly Ala Cys Val Asn Ala
            260                 265                 270
```

-continued

```
Met Asp Leu Trp Gln Phe Thr Pro Leu His Glu Ala Ala Ser Lys Asn
        275                 280                 285
Arg Val Glu Val Cys Ser Leu Leu Ser Tyr Gly Ala Asp Pro Thr
        290                 295                 300
Leu Leu Asn Cys His Asn Lys Ser Ala Ile Asp Leu Ala Pro Thr Pro
305                 310                 315                 320
Gln Leu Lys Glu Arg Leu Ala Tyr Glu Phe Lys Gly His Ser Leu Leu
                325                 330                 335
Gln Ala Ala Arg Glu Ala Asp Val Thr Arg Ile Lys Lys His Leu Ser
                340                 345                 350
Leu Glu Met Val Asn Phe Lys His Pro Gln Thr His Glu Thr Ala Xaa
                355                 360                 365
His Cys Ala Ala Ala Ser Pro Tyr Pro Lys Arg Lys Gln Ile Cys Glu
        370                 375                 380
Leu Leu Leu Arg Lys Gly Ala Xaa Ile Asn Glu Lys Thr Lys Glu Phe
385                 390                 395                 400
Leu Thr Pro Leu His Val Ala Ser Glu Lys Ala His Asn Asp Xaa Val
                405                 410                 415
Glu Val Val Lys His Glu Ala Lys Val Asn Ala Leu Asp Asn Leu
                420                 425                 430
Gly Gln Thr Ser Leu His Arg Ala Ala Tyr Cys Gly His Leu Gln Thr
        435                 440                 445
Cys Arg Leu Leu Ser Tyr Gly Cys Asp Pro Asn Ile Ile Ser Leu
450                 455                 460
Gln Gly Phe Thr Ala Leu Gln Met Gly Asn Glu Asn Val Gln Gln Leu
465                 470                 475                 480
Leu Gln Glu Gly Ile Ser Leu Gly Asn Ser Glu Ala Asp Arg Gln Leu
                485                 490                 495
Leu Glu Ala Ala Lys Ala Gly Asp Val Glu Thr Val Lys Lys Leu Cys
        500                 505                 510
Thr Val Gln Ser Val Asn Cys Arg Asp Ile Glu Gly Arg Gln Ser Thr
        515                 520                 525
Pro Leu His Phe Ala Ala Gly Tyr Asn Arg Val Ser Val Val Glu Tyr
        530                 535                 540
Leu Leu Gln His Gly Ala Asp Val His Ala Lys Asp Lys Xaa Xaa Leu
545                 550                 555                 560
Val Pro Leu His Asn Ala Cys Ser Tyr Gly His Tyr Glu Val Ala Glu
                565                 570                 575
Leu Leu Val Lys His Gly Ala Val Val Asn Val Ala Asp Leu Trp Lys
                580                 585                 590
Phe Thr Pro Leu His Glu Ala Ala Lys Gly Lys Tyr Glu Ile Cys
        595                 600                 605
Lys Leu Leu Leu Gln His Gly Ala Asp Pro Thr Lys Lys Asn Arg Asp
610                 615                 620
Gly Asn Thr Pro Leu Asp Leu Val Lys Asp Gly Asp Thr Asp Ile Gln
625                 630                 635                 640
Asp Leu Leu Arg Gly Asp Ala Ala Leu Leu Asp Ala Ala Lys Lys Ser
                645                 650                 655
Cys Leu Ala Arg Val Lys Lys Leu Ser Ser Pro Asp Asn Val Asn Cys
        660                 665                 670
Arg Asp Thr Gln Gly Arg His Ser Thr Pro Leu His Leu Ala Ala Gly
        675                 680                 685
Tyr Asn Asn Leu Glu Val Ala Glu Tyr Leu Leu Gln His Gly Ala Asp
```

-continued

```
            690                 695                 700
Val Asn Ala Gln Asp Lys Gly Gly Leu Ile Pro Leu His Asn Ala Ala
705                 710                 715                 720
Ser Tyr Gly His Val Asp Val Ala Ala Leu Leu Ile Lys Tyr Asn Ala
                725                 730                 735
Cys Val Asn Ala Thr Asp Lys Trp Ala Phe Thr Pro Leu His Glu Ala
                740                 745                 750
Ala Gln Lys Gly Arg Thr Gln Leu Cys Ala Leu Xaa Leu Ala His Gly
                755                 760                 765
Ala Asp Pro Thr Leu Lys Asn Gln Glu Gly Gln Thr Pro Leu Asp Leu
770                 775                 780
Val Ser Ala Asp Asp Val Ser Ala Leu Leu Thr Ala Ala Met Pro Pro
785                 790                 795                 800
Ser Ala Leu Pro Ser Cys Tyr Lys Pro Gln Val Leu Asn Gly Val Arg
                805                 810                 815
Ser Pro Gly Ala Thr Ala Asp Ala Leu Ser Ser Gly Pro Ser Ser Pro
                820                 825                 830
Ser Ser Leu Ser Ala Ala Ser Ser Leu Asp Asn Leu Ser Gly Ser Phe
                835                 840                 845
Ser Glu Leu Ser Ser Val Val Ser Ser Ser Gly Thr Glu Gly Ala Ser
850                 855                 860
Ser Leu Glu Lys Lys Glu Val Pro Gly Val Asp Phe Ser Ile Thr Gln
865                 870                 875                 880
Phe Val Arg Xaa Leu Gly Leu Glu His Leu Met Asp Ile Phe Glu Arg
                885                 890                 895
Glu Gln Ile Thr Leu Asp Val Leu Val Glu Met Gly His Lys Glu Leu
                900                 905                 910
Lys Glu Ile Gly Ile Asn Ala Tyr Gly His Arg His Lys Leu Ile Lys
                915                 920                 925
Gly Val Glu Arg Leu Ile Ser Gly Gln Gln Gly Leu Asn Pro Tyr Leu
930                 935                 940
Thr Leu Asn Thr Ser Gly Ser Gly Thr Ile Leu Ile Asp Leu Ser Pro
945                 950                 955                 960
Asp Asp Lys Glu Phe Gln Ser Val Glu Glu Met Gln Ser Thr Val
                965                 970                 975
Arg Glu His Arg Asp Gly Gly His Ala Gly Gly Ile Phe Asn Arg Tyr
                980                 985                 990
Asn Ile Leu Lys Ile Gln Lys Val Cys Asn Lys Lys Leu Trp Glu Arg
                995                 1000                1005
Tyr Thr His Arg Arg Lys Glu Val Ser Glu Glu Asn His Asn His
        1010                1015                1020
Ala Asn Glu Arg Met Leu Phe His Gly Ser Pro Phe Val Asn Ala
        1025                1030                1035
Ile Ile His Lys Gly Phe Asp Glu Arg His Ala Tyr Ile Gly Gly
        1040                1045                1050
Met Phe Gly Ala Gly Ile Tyr Phe Ala Glu Asn Ser Ser Lys Ser
        1055                1060                1065
Asn Gln Tyr Val Tyr Gly Ile Gly Gly Gly Thr Gly Cys Pro Val
        1070                1075                1080
His Lys Asp Arg Ser Cys Tyr Ile Cys His Arg Gln Leu Leu Phe
        1085                1090                1095
Cys Arg Val Thr Leu Gly Lys Ser Phe Leu Gln Phe Ser Ala Met
        1100                1105                1110
```

```
Lys Met Ala His Ser Pro Pro Gly His His Ser Val Thr Gly Arg
    1115                1120                1125

Pro Ser Val Asn Gly Leu Ala Leu Ala Glu Tyr Val Ile Tyr Arg
    1130                1135                1140

Gly Glu Gln Ala Tyr Pro Glu Tyr Leu Ile Thr Tyr Gln Ile Met
    1145                1150                1155

Arg Pro Glu Gly Met Val Asp Gly
    1160                1165

<210> SEQ ID NO 6
<211> LENGTH: 19
<212> TYPE: DNA
<213> ORGANISM: Artificial
<220> FEATURE:
<223> OTHER INFORMATION: PCR Primers

<400> SEQUENCE: 6
cccgagagct gttcgaggc                                              19

<210> SEQ ID NO 7
<211> LENGTH: 23
<212> TYPE: DNA
<213> ORGANISM: Artificial
<220> FEATURE:
<223> OTHER INFORMATION: PCR Primers

<400> SEQUENCE: 7
caatctttac tctgttatat cct                                         23

<210> SEQ ID NO 8
<211> LENGTH: 41
<212> TYPE: DNA
<213> ORGANISM: Artificial
<220> FEATURE:
<223> OTHER INFORMATION: PCR Primers

<400> SEQUENCE: 8
aagcggccgc attatggaaa ggatcatgtc gggtcgccgc t                     41

<210> SEQ ID NO 9
<211> LENGTH: 25
<212> TYPE: DNA
<213> ORGANISM: Artificial
<220> FEATURE:
<223> OTHER INFORMATION: PCR Primers

<400> SEQUENCE: 9
aaggatccac cataccttca ggcct                                       25

<210> SEQ ID NO 10
<211> LENGTH: 39
<212> TYPE: DNA
<213> ORGANISM: Artificial
<220> FEATURE:
<223> OTHER INFORMATION: PCR Primers

<400> SEQUENCE: 10
aaaagcttta tggaaaggat catgtcgggt cgccgctgc                        39
```